United States Patent
Ishihara et al.

(10) Patent No.: US 11,769,246 B2
(45) Date of Patent: Sep. 26, 2023

(54) PISTACHIO SORTING DEVICE

(71) Applicant: TOYO NUT Co., Ltd., Hyogo (JP)

(72) Inventors: Kazuya Ishihara, Hyogo (JP); Hiroto Nakajima, Hyogo (JP)

(73) Assignee: TOYO NUT CO., LTD., Hyogo (JP)

( * ) Notice: Subject to any disclaimer, the term of this patent is extended or adjusted under 35 U.S.C. 154(b) by 0 days.

(21) Appl. No.: 18/013,423

(22) PCT Filed: Jun. 11, 2021

(86) PCT No.: PCT/JP2021/022356
§ 371 (c)(1),
(2) Date: Dec. 28, 2022

(87) PCT Pub. No.: WO2022/259533
PCT Pub. Date: Dec. 15, 2022

(65) Prior Publication Data
US 2023/0196543 A1    Jun. 22, 2023

(51) Int. Cl.
*G06V 20/68*     (2022.01)
*G01N 33/02*     (2006.01)
(Continued)

(52) U.S. Cl.
CPC ....... *G06T 7/0004* (2013.01); *G01N 21/6456* (2013.01); *G01N 33/02* (2013.01);
(Continued)

(58) Field of Classification Search
CPC ........ G06T 7/0004; G06T 2207/10064; G06T 2207/30128; G01N 21/6456; G01N 33/02; G06V 10/255; G06V 10/26; G06V 20/68
(Continued)

(56) References Cited

U.S. PATENT DOCUMENTS 4,535,248 A     8/1985   Schade et al.
5,703,784 A  *  12/1997  Pearson ................. B07C 5/366
                                                    700/223
(Continued)

FOREIGN PATENT DOCUMENTS

JP    2009095758 A    5/2009
WO    0179834 A1      10/2001

OTHER PUBLICATIONS

Farsaie et al., "Design and Development of an Automatic Electro-Optical Sorter for Removing BGY Fluorescent Pistachio Nuts," Transactions of the ASAE, 24, 1372-1375, as early as Jan. 1981.
(Continued)

*Primary Examiner* — Sheela C Chawan
(74) *Attorney, Agent, or Firm* — Andrew L. Dunlap; Haynes Beffel & Wolfeld LLP

(57) ABSTRACT

A pistachio sorting device capable of accurately detecting BGY fluorescence emitted from a fluorescent material adhered to a shell of an in-shell pistachio to perform pass/fail determination and sort out defective products at high speed is provided. The pistachio sorting device comprises a lighting device 11 for irradiating in-shell pistachios which are objects to be sorted in an inspection region with ultraviolet light having a maximum peak wavelength within a range of 345 nm to 390 nm, an optical filter 12 for selectively transmitting light within a wavelength range of 500 nm to 600 nm, a sensor 13 for detecting a two-dimensional intensity distribution of the fluorescence transmitted through the optical filter 12 to generate two-dimensional image data indicating a two-dimensional intensity distribution of fluorescence in the inspection region, and a determining device for determining a pass/fail of for each object to be sorted 10 based on the two-dimensional image data.

14 Claims, 19 Drawing Sheets

(51) Int. Cl.
    *G06T 7/00*     (2017.01)
    *G06V 10/26*     (2022.01)
    *G01N 21/64*     (2006.01)
    *G06V 10/20*     (2022.01)

(52) U.S. Cl.
    CPC ............ *G06V 10/255* (2022.01); *G06V 10/26* (2022.01); *G06V 20/68* (2022.01); *G06T 2207/10064* (2013.01); *G06T 2207/30128* (2013.01)

(58) Field of Classification Search
    USPC .................. 382/100, 110; 209/577, 580, 587
    See application file for complete search history.

(56) References Cited

U.S. PATENT DOCUMENTS

| | | | | |
|---|---|---|---|---|
| 7,858,893 | B1* | 12/2010 | Haff | B07C 5/366 |
| | | | | 209/576 |
| 8,841,570 | B2* | 9/2014 | Vasilescu | G06T 7/0004 |
| | | | | 209/580 |
| 2010/0193412 | A1* | 8/2010 | Mack, Jr. | B07C 5/342 |
| | | | | 359/353 |
| 2012/0093985 | A1* | 4/2012 | Vasilescu | G06T 7/0004 |
| | | | | 382/110 |
| 2014/0142745 | A1* | 5/2014 | Johnston | B07C 5/36 |
| | | | | 700/223 |
| 2015/0174618 | A1* | 6/2015 | Soler Esteban | B07C 5/10 |
| | | | | 209/580 |

OTHER PUBLICATIONS

Hadavi, "Several physical properties of aflatoxin-contaminated pistachio nuts: Application of BGY fluorescence for separation of aflatoxin-contaminated nuts," Food Additives and Contaminants, Dec. 2005; 11 pages.
PCT Written Opinion of the International Searching Authority from PCT/JP2021/022356 dated Aug. 10, 2021, 3 pages.
Wu Q. et al., "Design and development of an on-line fluorescence spectroscopy system for detection of aflatoxin in pistachio nuts," Postharvest Biology and Technology, Sep. 18, 2019, vol. 159, 111016, <DOI: 10.1016/j.postharvbio.2019.111016>.
Hong et al., "Identification of Mildewed Peanuts by Computer Vision," China Academic Journal, Jan. 2008, 5 pages, English Abstract.

* cited by examiner

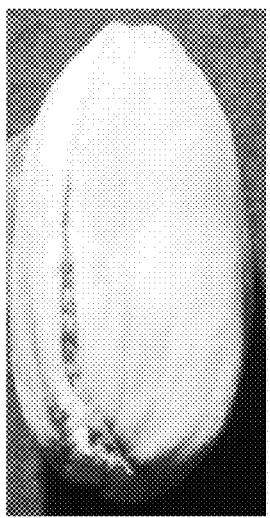
Outer shell (Visible light image: White light illumination)
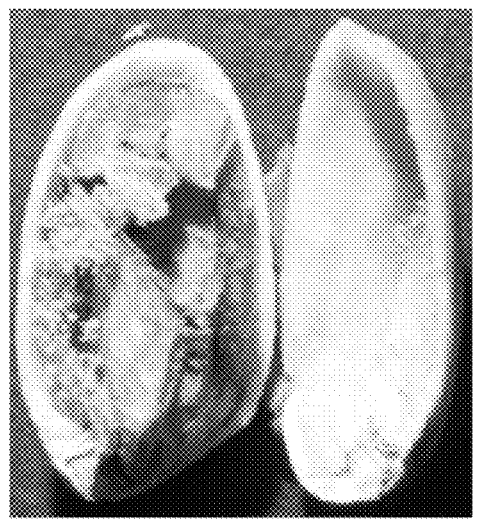
Inner shell (Visible light image: White light illumination)
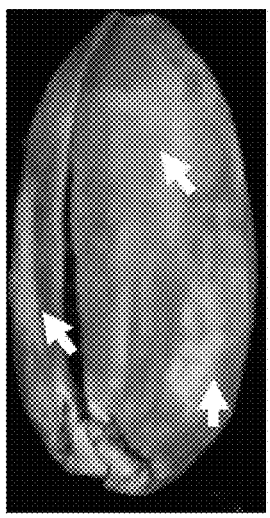
Outer shell (Fluorescent image: 365 nm ultraviolet light illumination)
Fig.3

Visible light image (White light illumination)
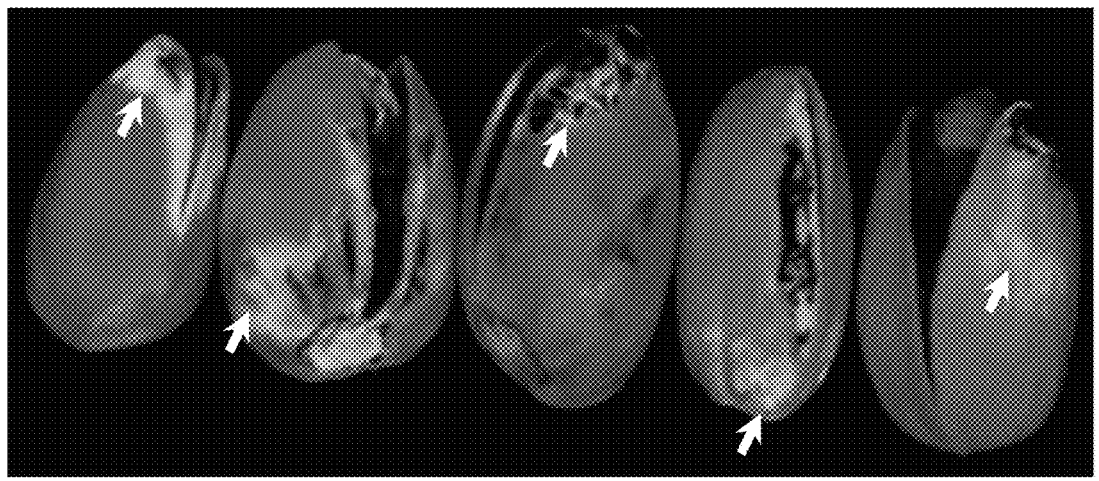
Fluorescent image (365 nm ultraviolet light illumination)
Fig. 4

Normal shell
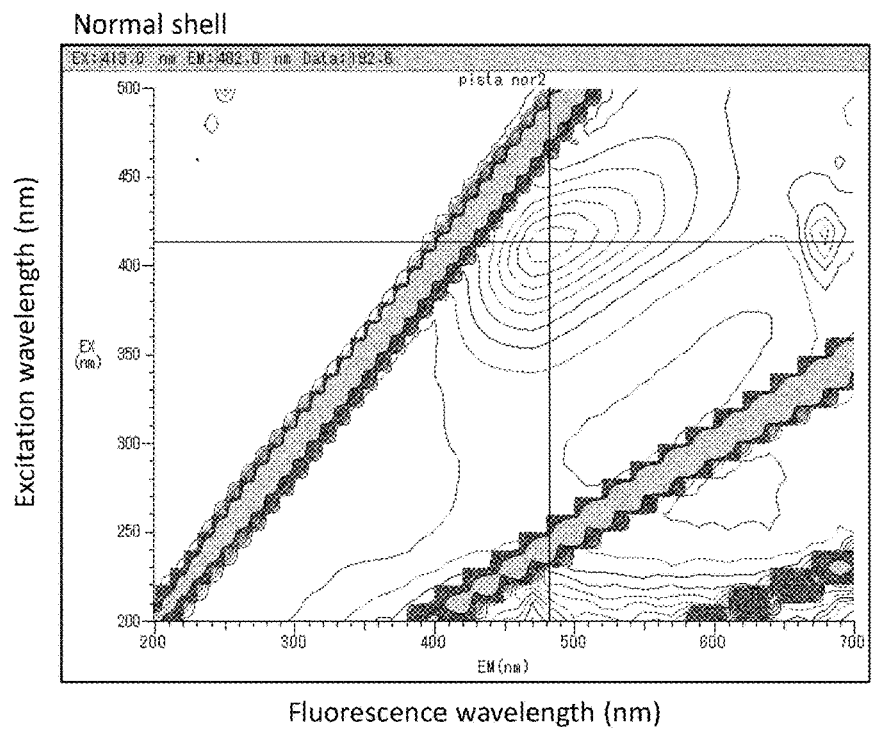
Fig. 5A
Abnormal shell
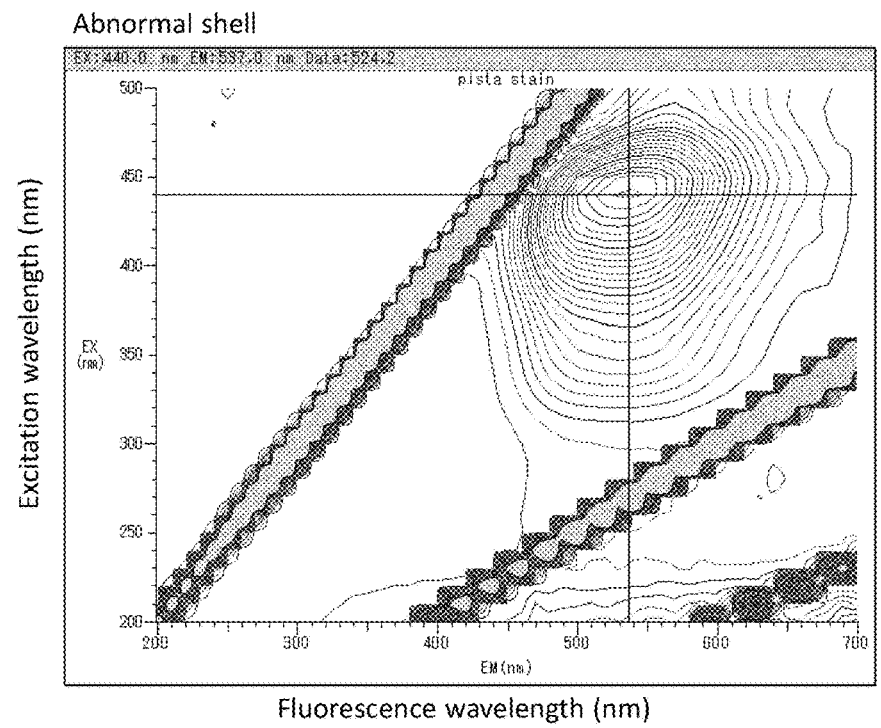
Fig. 5B
Fig. 5

PISTACHIO SORTING DEVICE

TECHNICAL FIELD

The present invention relates to a pistachio sorting device for sorting in-shell pistachios by determining whether insect damages, molds, physical damages, decay in a pistachio kernel, and stains on a pistachio shell are present based on images obtained by imaging the in-shell pistachios.

BACKGROUND ART

The pistachio of edible nuts has various deterioration in quality in the growth process and the like. For example, in the growing process, a navel orange worm (scientific name: Amyelois transitella) is attracted to an aroma component derived from a nut, and lays eggs on the mature pistachio hull. When the hull is damaged, an increase of phenolic byproducts in the hull causes pigments such as browning to adhere to the pistachio shell. Larvae hatched from eggs also feed on the pistachio kernel and grow. Because the cell walls of the kernel eaten by insects are destroyed, bacteria may easily enter the cell membrane from the outside, resulting in decay and mold generations.

Pistachio is not only externally damaged, but also cracked in the immature state of the kernel (early-split), and the inside of the hull may be cleaved, and the hull may be damaged. This damage increases the phenolic byproducts in the hull, and pigments such as browning are deposited on the pistachio shell, or the hull may decay, and molds may be generated due to this damage.

If the nuts damaged by insect pests and molds, etc. in the growing process are included, these damages spread, and molds are propagated to the normal nuts during storage. If the degraded pistachios are mixed into a product, not only will the consumer feel uncomfortable, but the manufacturer will also lose the consumer trust. Therefore, the damaged pistachios due to insect pests and diseases in the growth process are removed by color sorting and visual sorting at the stage of raw materials.

It has been reported that phenolic byproducts produced by damage during the growth process exhibit green to yellow fluorescence (bright green-yellow fluorescence, hereafter referred to as "BGY fluorescence") upon ultraviolet irradiation. Furthermore, in Non-Patent Document 1 described below, it is reported that there is a strong correlation between BGY fluorescence and the content of aflatoxin that is mycotoxin, and probability of detecting aflatoxin increases particularly when shell cleavage occurs in the early stage of growth.

In general, plants synthesize antimicrobial substance (phytochemicals) such as phenolic byproducts and flavonoids as secondary metabolites in order to prevent the invasion of bacteria from the outside when they are ingested by insects or physically damaged. If the physical damage is large, the antimicrobial substance cannot prevent the invasion of the bacteria, and decay progresses, and the mold fungi may propagate. BGY fluorescent materials are the ones in which phenolic byproducts of the secondary metabolite, which are phytochemicals formed by pistachio during growth, adhered to the shell, and when a large amount of the BGY fluorescent material adheres to the shell, the appearance is discolored and the commercial value is impaired, so that it is desired to remove it at the sorting stage of the raw materials.

PRIOR ART DOCUMENTS

Non-Patent Document

Non-Patent Document 1:
Ebrahim Hadavi, "Several physical properties of aflatoxin-contaminated pistachio nuts: Application of BGY fluorescence for separation of aflatoxin-contaminated nuts", Food Additives and Contaminants, November 2005; 22(11): 1144-53

Non-Patent Document 2:
A. Farsaie, W. F. McClure, and R. J. Monroe, "Design and development of an electro-optical sorter for removing BGY fluorescent pistachio nuts", Transactions of the ASAE, 24, 1372-1375 (1981)

SUMMARY OF THE INVENTION

Problems to be Solved by the Invention

Among edible nuts, pistachio is often provided to consumers in an in-shell state, and therefore it is necessary to accurately sort them in the in-shell state. However, the pistachio shell is pale yellow, and a portion of the shell is cleaved, so that pale green kernel and pale brown skin can be identified from the cleaved portion. When the in-shell pistachio is subjected to color sorting by a color sorter, it is difficult to determine a difference in color between the in-shell pistachio and the stain on the shell due to browning or the like to be removed. Particularly, it is extremely difficult to find insect damages of the inside kernel, since only the portions of the kernel where the shell is cleaved can be seen from the appearance.

By breaking the pistachio shell, it is possible to confirm the traces of insect damages produced in the kernel. However, since pistachio is vulnerable to humidity, flavor and taste tend to change without shells. As a result of this, the in-shell pistachio is widely accepted in general, and it is difficult to remove the shell.

As one of the sorting techniques of pistachios, a mechanical sorting technique using BGY fluorescence has been reported in Non-Patent Document 2 described above, but in order to accurately detect BGY fluorescence, it is required to sort pistachios one by one, so that a technique in which the sorting rate can withstand commercial use has not yet been sufficiently established.

In view of the foregoing problems, it is an object of the present invention to provide a pistachio sorting device capable of sorting pistachios at high speed by exciting a BGY fluorescent material adhered to a shell of pistachio with ultraviolet light and detecting BGY fluorescence to determine whether insect damages, molds, physical damages, decay in the kernel and stains adhered to the shell are present.

Means for Solving the Problem

In order to achieve the above object, the present invention provides a pistachio sorting device for sorting one or more in-shell pistachios, which are objects to be sorted, by detecting a fluorescent material adhered to a shell of an in-shell pistachio to determine a pass/fail for each object to be sorted. As the first feature, the pistachio sorting device comprises:

a lighting device for irradiating the objects to be sorted in an inspection region with ultraviolet light having a maximum peak wavelength within a range of 345 nm to 390 nm;

an optical filter for selectively transmitting light within a wavelength range of 500 nm to 600 nm;

a sensor for detecting a two-dimensional intensity distribution of fluorescence emitted from the objects to be sorted and transmitted through the optical filter to generate a two-dimensional image data indicating a two-dimensional intensity distribution of the fluorescence in the inspection region; and a determining device for determining a pass/fail for each object to be sorted based on the two-dimensional image data.

According to the pistachio sorting device of the first feature, by irradiating the ultraviolet light having the maximum peak wavelength within the range of 345 nm to 390 nm as the excitation light of the fluorescence generated from the object to be sorted, the fluorescence intensity is lower than the maximum intensity of the fluorescence obtained by the excitation light having a longer wavelength in both cases where the object to be sorted is normal and where the object to be sorted is abnormal, but the fluorescence intensity ratio between the cases where the object to be sorted is normal and where the object to be sorted is abnormal becomes high when each fluorescence is viewed in the wavelength range of 500 nm to 600 nm. Therefore, the pass/fail determination of the object to be sorted can be performed with high accuracy based on the two-dimensional image data indicating the two-dimensional intensity distribution in the inspection region of the fluorescence emitted from the object to be sorted.

Furthermore, even when the object to be sorted is either normal or abnormal, since the existence position of the object to be sorted in the inspection region can be identified by the two-dimensional intensity distribution of the fluorescence on the two-dimensional image data, it is possible to accurately determine whether the object to be sorted is normal or abnormal at each existence position in the inspection region.

Furthermore, it is preferable that the pistachio sorting device of the first feature includes a light shielding part that configures an inspection region inside and blocks entry of ambient light into the inspection region from outside.

According to the preferred implementation, when ultraviolet light as the excitation light irradiated by the lighting device and ambient light other than the fluorescence emitted from the object to be sorted are present in the space in which the pistachio sorting device is installed, by providing the light shielding part, the ambient light is not detected by the sensor, and deterioration of the accuracy of the pass/fail determination of the object to be sorted due to the ambient light can be prevented.

Furthermore, in the pistachio sorting device of the first feature, it is preferable that the lighting device irradiates the objects to be sorted in the inspection region with ultraviolet light having a maximum peak wavelength within a range of 350 nm to 375 nm.

According to the preferred implementation, it is possible to more accurately determine whether the object to be sorted is normal or abnormal at each existence position on the two-dimensional image data since the fluorescence intensity ratio between the cases where the object to be sorted is normal and where the object to be sorted is abnormal becomes higher within a wavelength range of 500 nm to 600 nm.

Furthermore, the present invention provides a pistachio sorting device having the second feature in addition to the first feature, wherein the determining device is configured to determine the pass/fail for each object to be sorted, based on the two-dimensional image data, in accordance with an area ratio between an area of an entire shell of an object to be sorted and an adhesion area of the fluorescent material to which a fluorescence intensity indicated by each pixel value of the two-dimensional image data within an existence range of the entire shell of the object to be sorted is equal to or larger than a predetermined threshold value.

The area of the entire shell of the object to be sorted is an area of the region surrounded by the outer edge of the entire shell in a single grain of the object to be sorted displayed on the two-dimensional image of the two-dimensional image data, and is an area of the front side of the entire shell of the object to be sorted displayed on the two-dimensional image and does not include an area of the back side not displayed on the two-dimensional image. If a part of the shell is cleaved, the area of the entire shell also includes the cleavage portion. Furthermore, the existence range of the entire shell is an extent surrounded by the outer edge of the entire shell displayed on the two-dimensional image.

According to the pistachio sorting device of the second feature, it is possible to identify the object to be sorted with a large adhesion area of the BGY fluorescent material as a defective product and to treat the object to be sorted having a small adhesion area of the BGY fluorescent material as a good product or a semi-good product.

Furthermore, the present invention provides a pistachio sorting device having the third feature in addition to the first feature, wherein the determining device is configured to determine the pass/fail for each object to be sorted, based on the two-dimensional image data, in accordance with the maximum value of the fluorescence intensity indicated by each pixel value of the two-dimensional image data of the objects to be sorted within an existence range of an entire shell of an object to be sorted in the inspection region.

According to the pistachio sorting device of the third feature, it is possible to identify the object to be sorted with a large fluorescence intensity of the BGY fluorescent material as a defective product, and to treat the object to be sorted as a good product or a semi-good product when the maximum fluorescence intensity of the BGY fluorescent material is not larger than the fluorescence intensity of the object to be sorted which is normal.

Furthermore, the present invention provides a pistachio sorting device having the fourth feature in addition to the first feature, wherein the determining device is configured to determine the pass/fail for each object to be sorted, based on the two-dimensional image data, in accordance with to an area ratio between an area of an entire shell of an object to be sorted and an adhesion area of the fluorescent material to which a fluorescence intensity indicated by each pixel value of the two-dimensional image data within an existence range of the entire shell of the object to be sorted is equal to or larger than a predetermined threshold value, and in accordance with the maximum value of the fluorescence intensity indicated by each pixel value of the two-dimensional image data of the objects to be sorted within the existence range of the entire shell of the object to be sorted in the inspection region.

According to the pistachio sorting device of the fourth feature, it is possible to identify the object to be sorted with a large adhesion area and a large fluorescence intensity of the BGY fluorescent material as a defective product, and treat the object to be sorted as a good product or a semi-good product when the adhesion area of the BGY fluorescent material is small, or when the maximum value of the fluorescence intensity of the BGY fluorescent material is not larger than the fluorescence intensity of the object to be sorted which is normal.

Furthermore, the present invention provides a pistachio sorting device having the fifth feature in addition to the second and fourth features, wherein the determining device is configured to perform pattern matching with a pre-registered geometric shape based on the two-dimensional image data, approximate an outer edge of the object to be sorted with the geometric shape, and calculate an area of the entire shell of the object to be sorted for each object to be sorted.

According to the pistachio sorting device of the fifth feature, even when there is a plurality of the objects to be sorted contacting each other in the inspection region, the respective outer edges of the objects to be sorted can be identified, and the respective areas of the entire shell of the objects to be sorted can be approximately calculated.

Furthermore, the present invention provides a pistachio sorting device having the sixth feature in addition to the third and fourth features, wherein the determining device is configured to perform pattern matching with a pre-registered geometric shape based on the two-dimensional image data, approximate an outer edge of the object to be sorted with the geometric shape, and calculate an existence range of the entire shell of the object to be sorted in the inspection region for each object to be sorted.

According to the pistachio sorting device of the sixth feature, even when there is a plurality of the objects to be sorted contacting each other in the inspection region, outer edges of the respective objects to be sorted can be identified, and existence ranges of the respective objects to be sorted in the inspection region can be approximately calculated.

Furthermore, in the pistachio sorting device of the fifth or sixth feature, when there is a plurality of the objects to be sorted in the inspection region, it is preferable that the determining device specifies a processing range excluding a range in which the object to be sorted that can be identified as the defective product cannot exist from the inspection region based on the two-dimensional image data, and the determining device performs the pattern matching in the processing range.

According to the preferred embodiment, when the objects to be sorted exist in large amounts in the inspection region and the defective product rate thereof is low, the processing times required for the pattern matching of determining device can be greatly reduced, and the processing capability of the pistachio sorting device is improved.

Furthermore, in the pistachio sorting device of any one of the first to fourth features, it is preferable that the determining device is configured to calculate a two-dimensional coordinate of a center of a geometric shape approximating an outer edge of the object to be sorted as a coordinate of a defective product in a two-dimensional coordinate indicating a position of the object to be sorted identified as the defective product in the inspection region.

According to the preferred embodiment, even when there is a plurality of the objects to be sorted contacting each other in the inspection region, the coordinates of defective products indicating the respective positions of the objects to be sorted identified as defective products in the inspection region can be approximately calculated.

Furthermore, in the pistachio sorting device of any one of the first to fourth features, it is preferable that the determining device is configured to calculate a two-dimensional coordinate indicating a position of the object to be sorted identified as a defective product in the inspection region as a coordinate of a defective product, and that the pistachio sorting device comprises a remover to remove the object to be sorted identified as the defective product based on the coordinate of the defective product calculated by the determining device.

According to the preferred embodiment, it is possible to remove the object to be sorted identified as the defective product from one or more in-shell pistachios which are one or more objects to be sorted present in the inspection region, and to automatically sort and collect only other good objects to be sorted.

Effect of the Invention

According to the pistachio sorting device of the above-described features, it is possible to determine, with high accuracy and at high speed, whether the object to be sorted is normal or abnormal at the respective existence positions in the inspection region based on the two-dimensional image data indicating the two-dimensional intensity distribution of the fluorescence emitted from the object to be sorted in the inspection region.

BRIEF DESCRIPTION OF THE DRAWINGS

FIG. 3 shows visible light images (by white light illumination) of the outer shell and the inner shell of in-shell pistachios with insect damages and a fluorescent image (by 365 nm ultraviolet light illumination) of the outer shell of an in-shell pistachio with insect damages.

FIG. 4 shows a visible light image and a fluorescent image of an early-split in-shell pistachio.

FIG. 5A is a graph showing a measurement result of the fluorescence properties (fluorescent fingerprint) of a normal object to be sorted measured by a spectrofluorometer.

FIG. 5B is a graph showing a measurement result of the fluorescence properties (fluorescent fingerprint) of an abnormal object to be sorted measured by a spectrofluorometer.

DESCRIPTION OF EMBODIMENT

Figure 1:
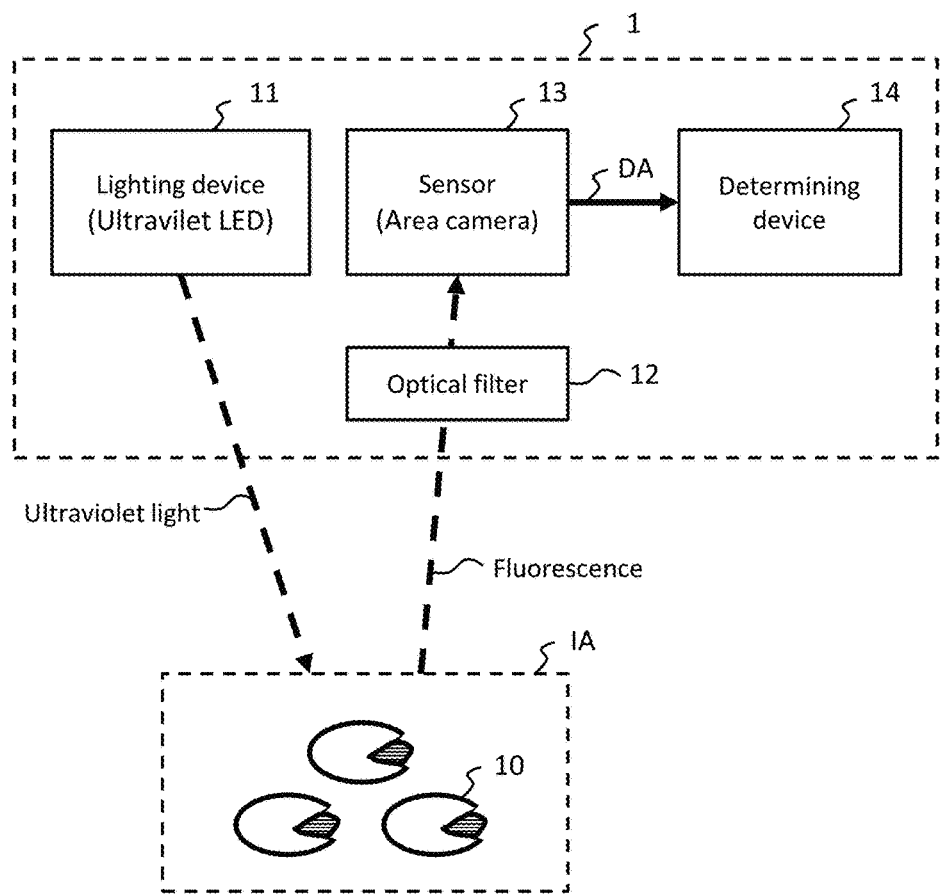
FIG. 1 is a block diagram illustrating an exemplary configuration of the pistachio sorting device according to the first embodiment.

The pistachio sorting device according to the embodiment of the present invention (hereinafter, simply referred to as "the present sorting device" as appropriate) is a device for determining whether insect damages, molds, physical damages, decay in the kernel and stains adhered to the shell are present based on the images obtained by imaging the in-shell pistachio. Hereinafter, the present sorting device will be described in detail with reference to the drawings. Incidentally, in the drawings showing the structural features of the present sorting device used in the following description, since content of the invention is schematically shown with emphasis on the main portion, for easy understanding of the description, the shape and dimensional ratio of each portion is not necessarily the same shape and dimensional ratio as the actual device. In addition, since the drawings using color photographs (FIGS. 3, 4, 11, and 12) are binarized to black and white for the application, the color information is missing.

First Embodiment

As shown in FIG. 1, the present sorting device 1 comprises a lighting device 11 for irradiating one or more in-shell pistachios which are one or more objects to be sorted 10 disposed in an inspection region IA with ultraviolet light, an optical filter 12 for selectively transmitting light within a predetermined wavelength range of fluorescence excited by the ultraviolet light irradiated from the lighting device 11 and emitted from the objects to be sorted 10, a sensor 13 for detecting a two-dimensional intensity distribution of the fluorescence transmitted through the optical filter 12 to generate two-dimensional image data DA indicating a two-dimensional intensity distribution of fluorescence in the inspection region IA, and a determining device 14 for determining a pass/fail for each object to be sorted 10 based on the two-dimensional image data DA.

Figure 2:
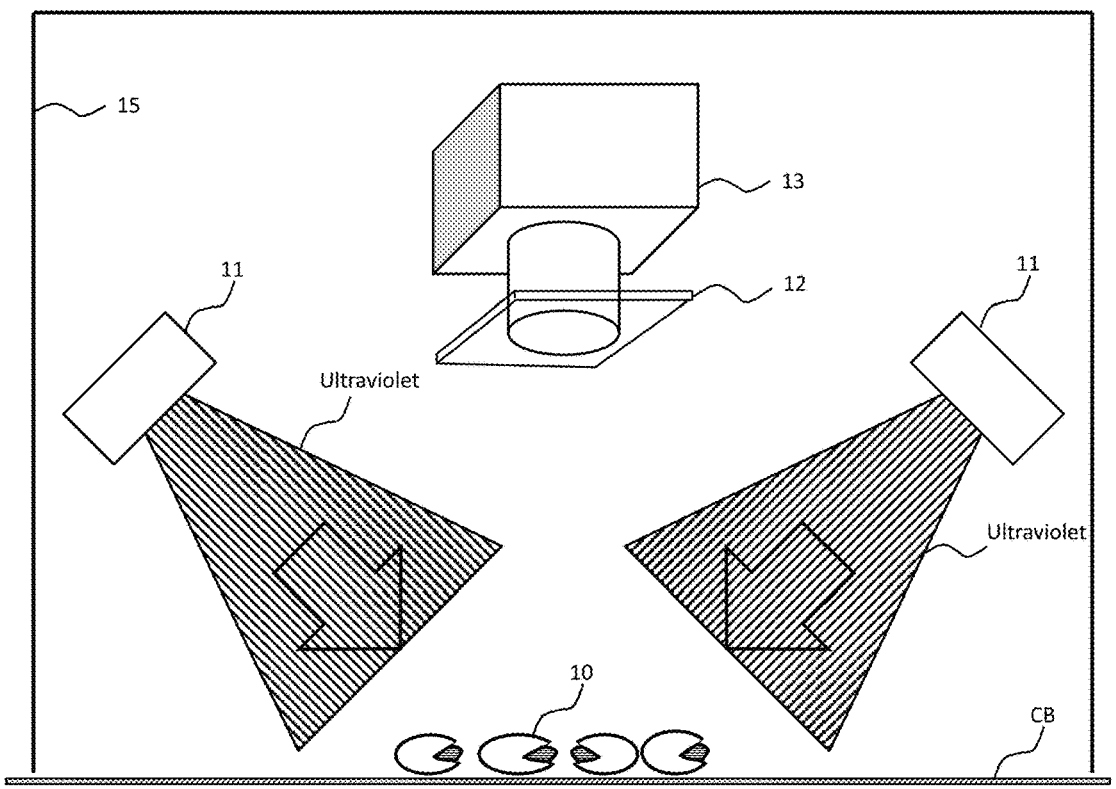
FIG. 2 is an explanatory diagram schematically illustrating positional relations between objects to be sorted, lighting devices, an optical filter, and a sensor in the exemplary configuration illustrated in FIG. 1.

In the present embodiment, as shown in FIG. 2, the objects to be sorted 10 are placed on a conveyor belt CB that conveys the objects to be sorted 10 from outside the inspection region IA through the inspection region IA to outside the inspection region IA. The belt surface of the conveyor belt CB is made of a material that does not emit fluorescence even when the ultraviolet light emitted from the lighting device 11 is received. In one implementation, the conveyor belt CB is 600 mm wide, and the moving speed of the conveyor belt CB is 100-150 mm/second.

In the present embodiment, the lighting device 11 is composed of an ultraviolet LED (Light Emitting Diode). In one implementation, four lighting devices 11 are installed at an elevation angle of 45° with respect to the belt surface of the conveyor belt CB to illuminate the inspection region IA on the belt surface from four directions. As for the directions in the plane parallel to the belt surface in the four directions, for example, it is preferable that each two directions are facing each other.

Each lighting device 11, for example, comprises twelve high-power ultraviolet LEDs, and the lighting devices 11 are configured to irradiate the objects to be sorted 10 in the inspection region IA from four directions with a total of forty-eight high-power ultraviolet LEDs. In FIG. 2, two of the four lighting devices 11 are schematically shown. In a preferred implementation, a diffuser lens is attached to the LED so that the ultraviolet light intensity in the inspection region IA is uniform. The maximum peak wavelength of the ultraviolet light emitted from the lighting device 11 is within a range of 345 nm to 390 nm, more preferably 350 nm to 375 nm. When the maximum peak wavelength is 365 nm, the ultraviolet illuminance within a illumination range of 50 cm×40 cm is 0.5 to 4 mW/cm$^2$, more preferably 1 to 2 mW/cm$^2$. In addition, if the variation of the ultraviolet illuminance in the inspection region IA is within ±15%, the pass/fail determination, which will be described later, can be performed without any problem.

Furthermore, in a preferred implementation, the four lighting devices 11 are configured so that each irradiation range is divided into a plurality of sections and the illuminance can be adjusted separately for each section. As a result, the illuminance in each irradiation range of the four lighting devices 11 is divided and adjusted according to the overlap of the irradiation ranges of the four lighting devices 11, and the variation in the ultraviolet illuminance in the inspection region IA can be easily controlled within ±15%. Incidentally, the variation of the ultraviolet illuminance within ±15% is one index, if the pass/fail determination described later can be performed without any problem, it is no problem that the variation of the ultraviolet illuminance may be greater than within ±15%.

Furthermore, in the present embodiment, each lighting device 11 is provided with a HOYA U360 ultraviolet transmission filter, so that a wavelength component of 400 nm or more of the ultraviolet light emitted from the ultraviolet LED is blocked.

The optical filter 12 is configured as a band-pass filter that selectively transmits lights in a wavelength range of 500 nm to 600 nm. In one implementation, the optical filter 12, which is a band-pass filter, is configured by combining a short-cut filter that blocks a wavelength of shorter than 500 nm (or a long-pass filter that transmits a wavelength of 500 nm or longer) and a long-cut filter that blocks a wavelength of longer than 600 nm (or a short-pass filter that transmits a wavelength of 600 nm or shorter).

In the optical filter 12, which is a band-pass filter, a transmission blocking band having an optical density (OD) of 2 or more (1% or less in terms of transmittance) is present in a wavelength range shorter than 500 nm and a wavelength range longer than 600 nm, respectively, and a transmission band having a transmittance of 80% or more, preferably 85% or more, and more preferably 90% or more is present in a wavelength range longer than 500 nm and shorter than 600 nm.

That is, the long wavelength end λ1 of the transmission blocking band BB1 on the short wavelength side is defined as λ1<500 nm, and the short wavelength end λ4 of the transmission blocking band BB2 on the long wavelength side is defined as λ4>600 nm. Furthermore, the short wavelength end λ2 of the transmission band BT is defined as λ2>500 nm, and the long wavelength end λ3 of the transmission band BT is defined as λ3<600 nm.

When the wavelength transitions from the transmission blocking band BB1 on the short wavelength side to the transmission band BT (the wavelength is increased from λ1 to λ2 through 500 nm), the transmittance transitions from 1% or less to the transmittance of the transmission band BT through 10%, 50%, and 80%. Here, the bandwidth at which the transmittance is increased from 15% to 85% of the maximum transmittance is 1 to 10 nm, preferably 1 to 5 nm. More preferably, 500 nm is present in the bandwidth.

When the wavelength transitions from the transmission band BT to the transmission blocking band BB2 on the long wavelength side (the wavelength is increased from λ3 to λ4 through 600 nm), the transmittance transitions from the transmittance of the transmission band BT to 1% or less through 80%, 50%, and 10%. Here, the bandwidth at which the transmittance is decreased from 85% to 15% of the maximum transmittance is 1 to 10 nm, preferably 1 to 5 nm. More preferably, 600 nm is present in the bandwidth.

Although the wavelengths λ1, λ2, λ3, and λ4 vary in accordance with variations in spectral characteristics (e.g., tolerances of cut-on/cut-off wavelengths, etc.) of the long-pass filter and the short-pass filter constituting the band-pass filter, they are present in the following ranges as an example.

480 nm≤λ1<500 nm, preferably 490 nm≤λ1<500 nm
500 nm<λ2≤520 nm, preferably 500 nm<λ2≤510 nm
580 nm≤λ3<600 nm, preferably 590 nm≤λ3<600 nm
600 nm<λ4≤620 nm, preferably 600 nm<λ4≤610 nm As described above, although the full width at half maximum of the band-pass band of the optical filter 12 (FWHM: bandwidth between the long wavelength side and the short wavelength side where the transmittance is a value of 50% (half maximum) of the maximum transmittance) may not necessarily be 100 nm (500 nm to 600 nm), it is present in the vicinity thereof (within about ±7 nm at the respective wavelength ends, preferably within about ±5 nm).

Next, Table 1 below shows the spectral characteristics and the like of the commercially available filters used in the example of the present embodiment as the long-pass filter and the short-pass filter constituting the optical filter 12 described above as a reference. All of them satisfy the above conditions. The spectral characteristics and the like of the long-pass filter and the short-pass filter are not limited to those shown in Table 1.

TABLE 1

| Items | Long-pass filter | Short-pass filter |
|---|---|---|
| Type | Dichroic | Dichroic |
| Transmission blocking band (nm) | 200-490 | 614-900 |
| Transmission band (nm) | 508-1650 | 350-587 |
| Optical density (OD) | ≥4 | ≥4 |
| Transmittance (%) | ≥91 | ≥91 |
| Cut-on/cut-off slopes (%) | <1 | <1 |
| Tolerances of cut-on/cut-off wavelengths (%) | ±1 | ±1 |

In the present embodiment, the sensor 13 is composed of an area camera. In one implementation of the area camera of the sensor 13, a monochrome CCD camera having 5M pixels (2488 pixels in horizontal direction×2055 pixels in vertical direction) can be suitably used. Furthermore, the optical filter 12 is attached in front of the light receiving opening of the sensor 13, so that the sensor 13 can selectively receive light in the wavelength range of 500 nm to 600 nm of fluorescence emitted from the objects to be sorted 10.

The two-dimensional image data DA generated by the sensor 13 composed of the monochrome CCD camera having 5 M pixels (2488 pixels×2055 pixels) in the above implementation are gray-scale image data in which each pixel of 5 M pixels (2488 pixels×2055 pixels) has a received light intensity of 8-bit gray-scale (0 to 255 gray-scale). The horizontal direction of the two-dimensional image data DA frame is parallel to the width direction of the conveyor belt CB, and the vertical direction is parallel to the traveling direction of the conveyor belt CB.

In the present embodiment, as an example, light reception sensitivity of sensor 13, aperture of lens, and the like are adjusted in accordance with the ultraviolet illuminance in the inspection region IA and the transmittance characteristics of the optical filter 12, in order that each pixel value (gray-scale value) of the two-dimensional image data DA indicating the fluorescence intensity of the BGY fluorescence emitted from the defective object to be sorted 10 is 125 or more, each pixel value (gray-scale value) of the two-dimensional image data DA indicating the fluorescence intensity of the cell wall-derived fluorescence emitted from the shell of the normal object to be sorted 10 is 40 or more, and each pixel value (gray-scale value) of the belt surface of the conveyor belt CB which is a background of two-dimensional image of the inspection region IA is approximately around 20. The reason why the gray-scale value of the belt surface of the conveyor belt CB is not zero is due to the reflection of the fluorescence emitted from the object to be sorted 10 on the belt surface or the reflection of weak ambient light entering the lightproof box 15 described later. When the area camera used for the sensor 13 has a 10-bit gray-scale, for example, instead of an 8-bit gray-scale, the respective gray-scale values are increased by about four times according to the sensitivity characteristics of the area camera to be used.

In the present embodiment, the lighting device 11, the optical filter 12, and the sensor 13 are installed in the lightproof box 15, and the entry of ambient light into the inspection region IA is blocked. Here, the ambient light is the light coming from the outside of the present sorting device 1 other than the ultraviolet light emitted from the lighting device 11 and the fluorescence excited by the ultraviolet light.

However, openings are provided at upstream and downstream sides of the conveyor belt CB so that the objects to be sorted 10 placed on the conveyor belt CB can enter from the outside of the lightproof box 15 into the lightproof box 15 and exit out of the lightproof box 15 in accordance with the movement of the conveyor belt CB. It is preferable that the entry of the environment light through the openings into the inspection region IA is completely blocked, but if the total noise level of the ambient light itself and the fluorescence emitted by the ambient light due to the entry of the weak ambient light is, for example, about 10 or less in the 8-bit gray-scale, that is, if the total noise level is a level such that the fluorescence intensity (a gray-scale value of about 40) of the cell wall-derived fluorescence emitted from the shell of the normal object to be sorted 10 is sufficiently distinguishable, it is permissible for the ambient light to enter as weakly as the noise level.

In other words, when the interior of the room in which the present sorting device 1 is installed is illuminated so that the ambient light in the room contains no or almost no light with wavelength components of 500 nm to 600 nm or wavelength components of 600 nm or less, and the noise level is, for example, a gray-scale value of about 10 or less, the lighting device 11, the optical filter 12, and the sensor 13 do not necessarily have to be installed in the lightproof box 15.

Next, an anomaly of the object to be sorted 10 which is an object to be inspected in the present embodiment will be briefly described. FIG. 3 shows visible light images (by white light illumination) of the outer shell and the inner shell of in-shell pistachios with insect damages and a fluorescent image (by 365 nm ultraviolet light illumination) of the outer shell of in-shell pistachio with insect damages. The kernel inside the shell is damaged by orange-worm larvae, and BGY fluorescent material generated from the kernel adheres to the inside of the shell and reaches the outside of the shell. This BGY fluorescent material can be easily detected from the outside of the shell in the fluorescent image (see arrows).

FIG. 4 shows a visible image and a fluorescent image of an early-split in-shell pistachio. In the early stage of ripening of the hull, the inner shell cracks and cracks occur in the hull, so that the phenolic compound adheres to the shell from the hull, or the hull is damaged by insects, so that the phenolic compound is generated from the hull and adheres to the shell, or the insects lay eggs on the hull and the hull and the kernel are damaged, so that the phenolic compound is generated from the hull and adheres to the shell, or the internal kernel is eaten by the larvae of the orange worm, so that the phenolic compound is generated from the kernel and diffuses from the inside of the shell to the outside of the shell. When this phenolic compound is irradiated with ultraviolet light, it emits visible BGY fluorescence. This phenolic compound can be easily detected from the outside of the shell in the fluorescent image (see arrows).

Next, the reason why the maximum peak wavelength of the ultraviolet light irradiated from the lighting device 11 is set within a range of 345 nm to 390 nm, more preferably a range of 350 nm to 375 nm, the wavelength components of the ultraviolet light which are equal to or longer than 400 nm are blocked, and the wavelength range received by the sensor 13 (the transmission wavelength range of the optical filter 12) is set to 500 nm to 600 nm will be described.

In order to select the optimal fluorescence for sorting the in-shell pistachios, the respective fluorescence properties were investigated to the normal object to be sorted 10 and the abnormal object to be sorted 10 having anomalies such as insect damages, molds, physical damages, decay in the kernel and stains adhered to the shell, using a spectrofluorometer (Hitachi F-7000). FIGS. 5A and 5B show the measurement results by the spectrofluorometer. FIG. 5A shows the measurement results of the normal object to be sorted 10, and FIG. 5B shows the measurement results of the abnormal object to be sorted 10.

In FIGS. 5A and 5B, the excitation wavelength is represented by a vertical axis, the fluorescence wavelength is represented by a horizontal axis, and the fluorescence intensities are represented by contour lines. In FIGS. 5A and 5B, although a part of the fluorescence intensity information is missing because the contour lines originally displayed in color are binarized into black and white for the application, the portion where the contour lines closed by surrounding the same point in FIGS. 5A and 5B are narrowed has the maximum fluorescence intensity at the top portion (the same point). FIGS. 5A and 5B are called a fluorescent fingerprint because they look like a fingerprint of a human finger.

Fluorescence is observed at a longer wavelength than the excitation wavelength (Stokes's law), so a fluorescent fingerprint appears in the lower right part of the diagonal. Furthermore, since the fluorescence wavelength does not change even if the excitation wavelength is changed if the fluorescent material is the same component, the fluorescence intensity is drawn in a closed contour line surrounding the same point. Fluorescence from the shell of the normal object to be sorted 10 (normal shell fluorescence) exhibits blue fluorescence with maximum fluorescence intensity at about 480 nm fluorescence wavelength when excited with about 410 nm light. On the other hand, when excited with about 440 nm light, fluorescence from the abnormal object to be sorted 10 exhibits BGY fluorescence in which fluorescence intensity is maximized at a fluorescence wavelength of about 540 nm. A spectrum of the BGY fluorescence shows a broad spectrum in a blue-green-yellow range of 450 nm to 600 nm.

FIGS. 6A to 6C show cross-sectional shapes (fluorescence spectra) of three kinds of excitation light wavelengths of contour lines shown in FIG. 5A and FIG. 5B. In FIGS. 6A to 6C, the spectra of the BGY fluorescence of the abnormal object to be sorted 10 are indicated by filled triangles (▲), and the spectra of the normal shell fluorescence of the normal object to be sorted 10 are indicated by open circles (○), the relative fluorescence intensity is indicated by the vertical axis, and the fluorescence wavelength is indicated by the horizontal axis. FIG. 6A shows a fluorescence spectrum in which the wavelength of the excitation light is 360 nm, FIG. 6B shows a fluorescence spectrum in which the wavelength of the excitation light is 410 nm, and FIG. 6C shows a fluorescence spectrum in which the wavelength of the excitation light is 440 nm. It can be seen from FIGS. 6A to 6C that, even if the wavelength of the excitation light increases, the maximum peak wavelength of the BGY fluorescence is almost constant around 530 nm (520 nm to 540 nm), and only the fluorescence intensity increases, while the maximum peak wavelength of the normal shell fluorescence increases to 460 nm, 480 nm, and 520 nm as the excitation light wavelength increases to 360 nm, 410 nm, and 440 nm, approaching the maximum peak wavelength of the BGY fluorescence. In FIGS. 6A to 6C, the wavelength components of the excitation light are displayed as a part of BGY fluorescence and the normal shell fluorescence.

As shown in FIGS. 6A to 6C, it is preferable that the maximum peak wavelength (520 nm~540 nm) of the BGY fluorescence is included in the transmission wavelength range of the optical filter 12. In addition, it is not required that the maximum peak wavelength of the fluorescence intensity of the normal shell fluorescence is included in the transmission wavelength range of the optical filter 12, but a part of wavelength range in which the fluorescence intensity of the normal shell fluorescence is equal to or higher than a certain value should be included because it is necessary to specify the position or the presence range of the object to be sorted 10.

Figure 6:
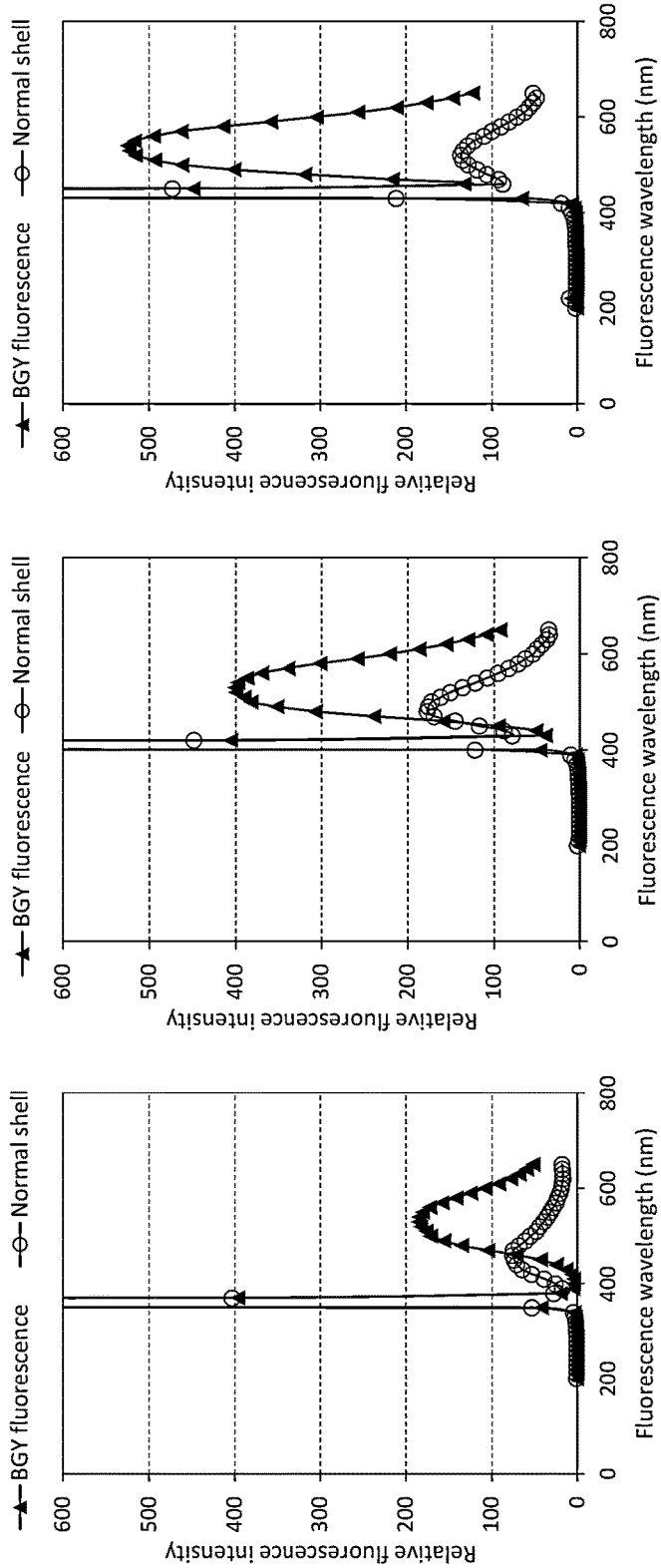
FIGS. 6A to 6C show spectral diagrams illustrating cross-sectional shapes (fluorescence spectrum) of contour lines shown in FIG. 5A and FIG. 5B superimposed on each other at three kinds of excitation light wavelengths.
Figure 7:
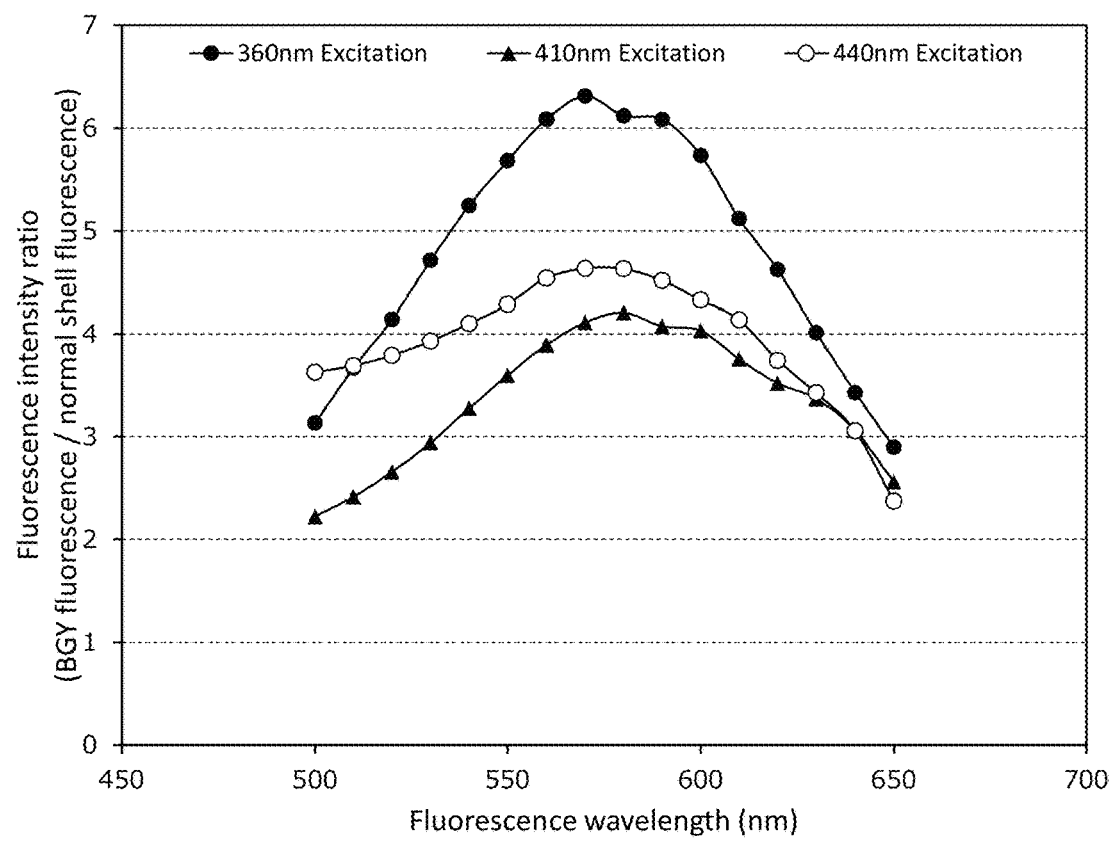
FIG. 7 is a graph showing fluorescence wavelength dependencies of three kinds of fluorescence intensity ratios of BGY fluorescence and normal shell fluorescence (BGY fluorescence/normal shell fluorescence) with different excitation-light wavelengths.

FIG. 7 shows the fluorescence wavelength dependency of the fluorescence intensity ratio (BGY fluorescence/normal shell fluorescence) between the BGY fluorescence and the normal shell fluorescence when the wavelength of the excitation light is 360 nm, 410 nm, and 440 nm. The fluorescence intensity ratio is indicated by the vertical axis, and the fluorescence wavelength is indicated by the horizontal axis. The fluorescence intensity ratio is calculated from the relative fluorescence intensity shown in FIGS. 6A to 6C. The fluorescence intensity ratio is largest when the wavelength of the excitation light is 360 nm among the three wavelengths. When the fluorescence wavelength is around 570 nm in particular, the fluorescence intensity ratio is maximized and SN ratio between the BGY fluorescence and the normal shell fluorescence is increased.

In addition, similarly to the case where the maximum peak wavelength of the BGY fluorescence is substantially constant around 530 nm with respect to the change in the wavelength of the excitation light, the fluorescence wavelength at which the fluorescence intensity ratio is maximum is also substantially constant around 570 nm (570 nm to 580 nm) with respect to the change in the wavelength of the excitation light. Therefore, it is preferable that the fluorescence wavelength (570 nm to 580 nm) at which the fluorescence intensity ratio is maximized is also included together with the maximum peak wavelength (520 nm to 540 nm) of the BGY fluorescence in the transmission wavelength range of the optical filter 12.

Figure 8:
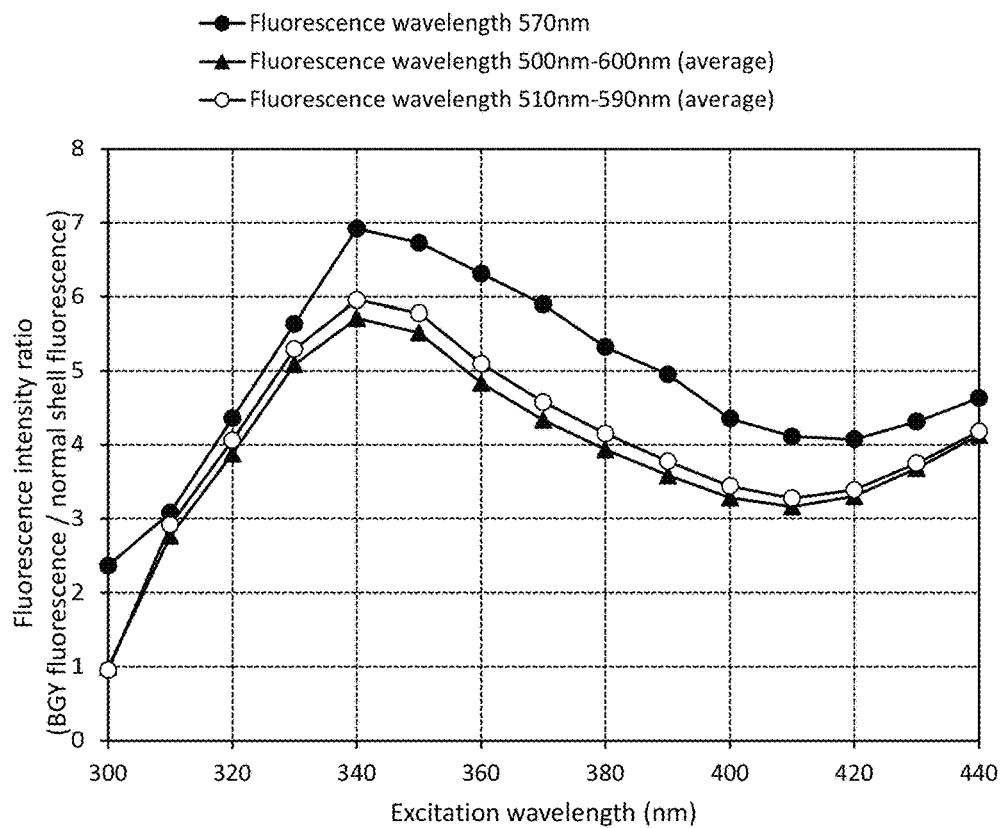
FIG. 8 is a graph showing excitation-light wavelength dependencies of three kinds of fluorescence intensity ratios of BGY fluorescence and normal shell fluorescence with different fluorescence wavelengths.

FIG. 8 shows the excitation light wavelength dependence of the fluorescence intensity ratio for the fluorescence intensity ratio of the BGY fluorescence and the normal shell fluorescence at the fluorescence wavelength of 570 nm (BGY fluorescence/normal shell fluorescence, hereinafter referred to as "the first fluorescence intensity ratio (Rf1)"), the fluorescence intensity ratio of the average fluorescence intensity of each 9 points at the fluorescence wavelengths of 510 nm to 590 nm (10 nm intervals) (mean BGY fluorescence/mean normal shell fluorescence, hereinafter referred to as "the second fluorescence intensity ratio (Rf2)"), and the fluorescence intensity ratio of the average fluorescence intensity of each 11 points at the fluorescence wavelengths of 500 nm to 600 nm (10 nm intervals) (mean BGY fluorescence/mean normal shell fluorescence, hereinafter referred to as "the third fluorescence intensity ratio (Rf3)"). The wavelength of the excitation light is varied within a range of 300 nm to 440 nm. The fluorescence intensity ratio is indicated by the vertical axis, and the wavelength of the excitation light is indicated by the horizontal axis. The first and second fluorescence intensity ratios are calculated from the measurement results shown in FIGS. 5A and 5B.

The first fluorescence intensity ratio is greater than or equal to about 5.0 when the wavelength of the excitation light is in the range of about 325 nm to about 390 nm and is greater than the fluorescence intensity ratio when the wavelength of the excitation light is in the range of 400 nm to 440 nm. The second fluorescence intensity ratio is greater than or equal to about 4.4 when the wavelength of the excitation light is in the range of about 325 nm to about 375 nm and is greater than the fluorescence intensity ratio when the wavelength of the excitation light is in the range of 380 nm to 440 nm. The third fluorescence intensity ratio is greater than or equal to about 4.1 when the wavelength of the excitation light is in the range of about 325 nm to about 375 nm and is greater than the fluorescence intensity ratio when the wavelength of the excitation light is in the range of 380 nm to 440 nm. All the first to third fluorescence intensity ratios are maximized in particular when the wavelength of the excitation light is around 340 nm, and SN ratio between the BGY fluorescence and the normal shell fluorescence is increased.

From FIG. 8, since all of the first to third fluorescence intensity ratios sharply decrease when the wavelength of the excitation light is below 340 nm, assuming the use of ultraviolet LED as the light source of the excitation light, when the full width at half maximum (FWHM) of the emission spectrum is about 10 nm to 20 nm, it is preferable that the maximum peak wavelength of the ultraviolet light irradiated by the lighting device 11 is 345 nm or more. On the other hand, even if the wavelength of the excitation light exceeds 390 nm by about 5 nm, all the first to third fluorescence intensity ratios do not significantly decrease, so that there is no significant problem even if the maximum peak wavelength of the ultraviolet light irradiated by the lighting device 11 is equal to or less than 390 nm. Therefore, the maximum peak wavelength of the ultraviolet light irradiated by the lighting device 11 is preferably within the range of 345 nm to 390 nm, and more preferably within the range of 350 nm to 375 nm, from the viewpoint of SN ratio between the BGY fluorescence and the normal shell fluorescence.

Furthermore, as described above, since the maximum peak wavelength of the BGY fluorescence is substantially constant around 530 nm, even if the wavelength of the excitation light is increased, when the maximum peak wavelength of the excitation light is increased beyond 400 nm, not only the fluorescence intensity ratio decreases, resulting in a decrease in SN ratio, but also the wavelength of the excitation light and the wavelength of the BGY fluorescence are close to each other, so that it is difficult to separate the excitation light and the reflected light thereof from the BGY fluorescence. Therefore, it is preferable that the maximum peak wavelength of the ultraviolet light irradiated by the lighting device 11 is within the range of 345 nm to 390 nm.

Incidentally, as shown in FIG. 6, both fluorescence intensities of the BGY fluorescence and the normal shell fluorescence tend to decrease as the wavelength of the excitation light becomes shorter. Therefore, when the fluorescence intensity of the normal shell fluorescence is excessively decreased, it is necessary to take care of the excessive decrease by using a highly sensitive sensor as the sensor 13. However, it is not particularly problematic if the maximum peak wavelength of the exciting light is equal to or greater than 345 nm.

Figure 9:
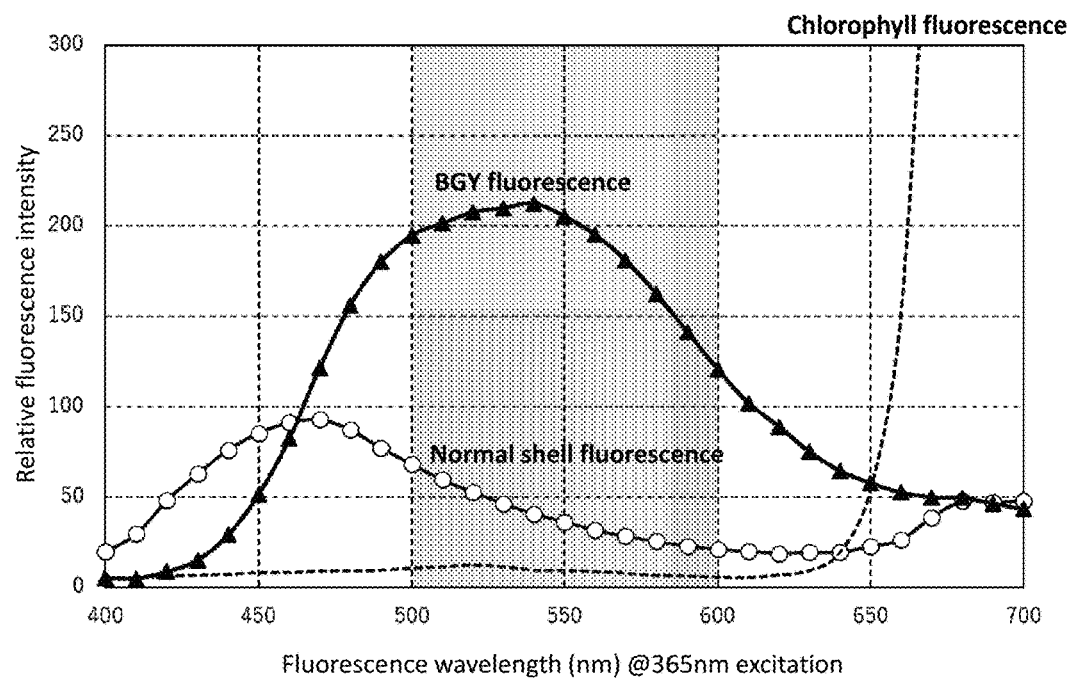
FIG. 9 is a spectral diagram showing respective fluorescence spectra of normal shell fluorescence of the object to be sorted 10, BGY fluorescence of the abnormal object to be sorted 10 with insect damages, and fluorescence emitted from the kernel when irradiated with excitation light with a wavelength of 365 nm.

FIG. 9 shows respective fluorescence spectra of the normal shell fluorescence of the normal object to be sorted 10, the BGY fluorescence of the abnormal object to be sorted 10 with insect damages, and the fluorescence emitted from the kernel when irradiated with the excitation light with a wavelength of 365 nm. The relative fluorescence intensity is indicated by the vertical axis, and the fluorescence wavelength is indicated by the horizontal axis. The normal shell fluorescence is a cell-wall-derived fluorescence, and the BGY fluorescence is derived from the fact that phenolic compound is produced from the hull and kernel of the pistachio and adhered to the shell when the hull and kernel are physically damaged or damaged by insect.

In addition, in the in-shell pistachio of the object to be sorted 10, a portion of the shell is cleaved, and a light green kernel and a light brown skin are exposed from the cleaved portion. When this kernel is irradiated with ultraviolet light, chlorophyll contained in the kernel is excited, and red fluorescence with the maximum peak wavelength of 685 nm is emitted. For this reason, when the kernel inside the cleaved portion of the in-shell pistachio is irradiated with ultraviolet light, as in the case of the BGY fluorescence, strong chlorophyll fluorescence is expressed. Therefore, a wavelength component having a large fluorescence intensity of the chlorophyll fluorescence needs to be separated from the BGY fluorescence of the abnormal object to be sorted 10. The fluorescence intensity of the chlorophyll fluorescence in a range of the fluorescence wavelength of 480 nm to 620 nm is as low as about 10% to about 35% of the fluorescence intensity of the normal shell fluorescence.

According to the above description, in the present embodiment, the transmission wavelength range of the optical filter 12 is set to from 500 nm to 600 nm so as to include the maximum peak wavelength (520 nm to 540 nm) of the BGY fluorescence and the wavelength (570 nm to 580 nm), at which the light intensity ratio of the BGY fluorescence and the normal shell fluorescence (BGY fluorescence/normal shell fluorescence) is maximized, and to completely separate the chlorophyll fluorescence from the BGY fluorescence.

Here, with respect to the upper limit of the transmission wavelength range of the optical filter 12, when the upper limit is increased beyond 600 nm, the fluorescence intensity ratio of the BGY fluorescence and the normal shell fluorescence is sharply decreased from FIG. 7. Therefore, in the present embodiment, the upper limit value is set to 600 nm in order to separate the chlorophyll fluorescence from the BGY fluorescence completely and to ensure the SN ratio between the BGY fluorescence and the normal shell fluorescence.

On the other hand, the maximum peak wavelength of the normal shell fluorescence is increased as the wavelength of the excitation light is increased, but it is less than or equal to 470 nm when the maximum peak wavelength of the excitation light is below 390 nm. Therefore, the fluorescence intensity of the normal shell fluorescence will gradually decrease as the fluorescence wavelength is increased beyond 470 nm. As described above, since it is necessary to specify the position or the existence range of the object to be sorted 10, a part of the wavelength range in which the fluorescence intensity of the normal shell fluorescence is equal to or higher than a certain value should be included in the transmission wavelength range of the optical filter 12. Therefore, the lower limit of the transmission wavelength range of the optical filter 12 is preferably shorter than the maximum peak wavelength of the BGY fluorescence (520 nm to 540 nm) and is preferably 500 nm or less. However, since the fluorescence intensity ratio of the BGY fluorescence and the normal shell fluorescence decreases to 2 or less when the fluorescence wavelength is reduced below 500 nm within the wavelength range of 340 nm to 390 nm of the excitation light, the fluorescence wavelength is preferably 500 nm or more in order to ensure the SN ratio between the BGY fluorescence and the normal shell fluorescence. Therefore, in the present embodiment, the lower limit of the transmission wavelength range of the optical filter 12 is set to 500 nm.

More specifically, as described above, the long wavelength end $\lambda 1$ of the transmission blocking band BB1 on the short wavelength side, the short wavelength end $\lambda 2$ and the long wavelength end $\lambda 3$ of the transmission band BT, and the short wavelength end $\lambda 4$ of the transmission blocking band BB2 on the long wavelength side of the optical filter 12 are set as 480 nm$\leq \lambda 1<$500 nm, 500 nm$<\lambda 2<$520 nm, 580 nm$\leq \lambda 3<$600 nm, 600 nm$<\lambda 4\leq$620 nm. Therefore, since the maximum peak wavelength of the BGY fluorescence (520 nm to 540 nm) and the fluorescence intensity ratio of the BGY fluorescence and the normal shell fluorescence (BGY fluorescence/normal shell fluorescence) are included in the transmission band BT, the fluorescence wavelength within the wavelength range is transmitted with high transmittance and is received by the sensor 13. In addition, in the chlorophyll fluorescence, a wavelength component of 640 nm or more in which the fluorescence intensity is sharply increased is blocked being attenuated to 1% or less by the transmission blocking band BB2 on the long wavelength side.

Furthermore, when the long wavelength end $\lambda 1$ of the transmission blocking band BB1 on the short wavelength side decreases to 480 nm, the sensor 13 receives fluorescence of a wavelength component with a fluorescence intensity ratio of the BGY fluorescence and the normal shell fluorescence as low as 2 or less. But since the transmittance for the wavelength component is significantly lower than that of the transmission band BT, and becomes lower in particular as the wavelength becomes shorter such that the fluorescence intensity ratio is even lower, the effect on the SN ratio between the BGY fluorescence and the normal shell fluorescence is limited, and it is not problematic to determine the pass/fail for each object to be sorted 10 by the determining device 14 described later.

As described above, the pass/fail determination of the object to be sorted 10 can be performed within the variation ranges of the respective wavelengths $\lambda 1$, $\lambda 2$, $\lambda 3$, and $\lambda 4$.

As described above, in the present embodiment, the lighting device 11 is provided with an ultraviolet transmission filter which blocks a wavelength component of 400 nm or more. Thus, even if the maximum peak wavelength of the ultraviolet light emitted from the lighting device 11 is within a range of 345 nm to 390 nm, when a wavelength component of 400 nm or more is included, generation of fluorescence excited by the wavelength component of 400 nm or more is suppressed, and deterioration in the SN ratio between the BGY fluorescence and the normal shell fluorescence due to this fluorescence can be prevented.

It should be noted that the lighting device is not necessarily provided with the U360 ultraviolet transmission filter described above, when the emission intensity of the wavelength component of 400 nm or higher emitted from the lighting device 11 is small, and for example, the fluorescence intensity in the wavelength range of 500 nm to 600 nm of the fluorescence excited by the wavelength component of 400 nm or higher is sufficiently smaller (for example, 10% or less, preferably 5% or less) than the fluorescence intensity in the wavelength range of 500 nm to 600 nm of the fluorescence excited by the wavelength component of 400 nm or lower emitted from the lighting device 11.

Figure 10:
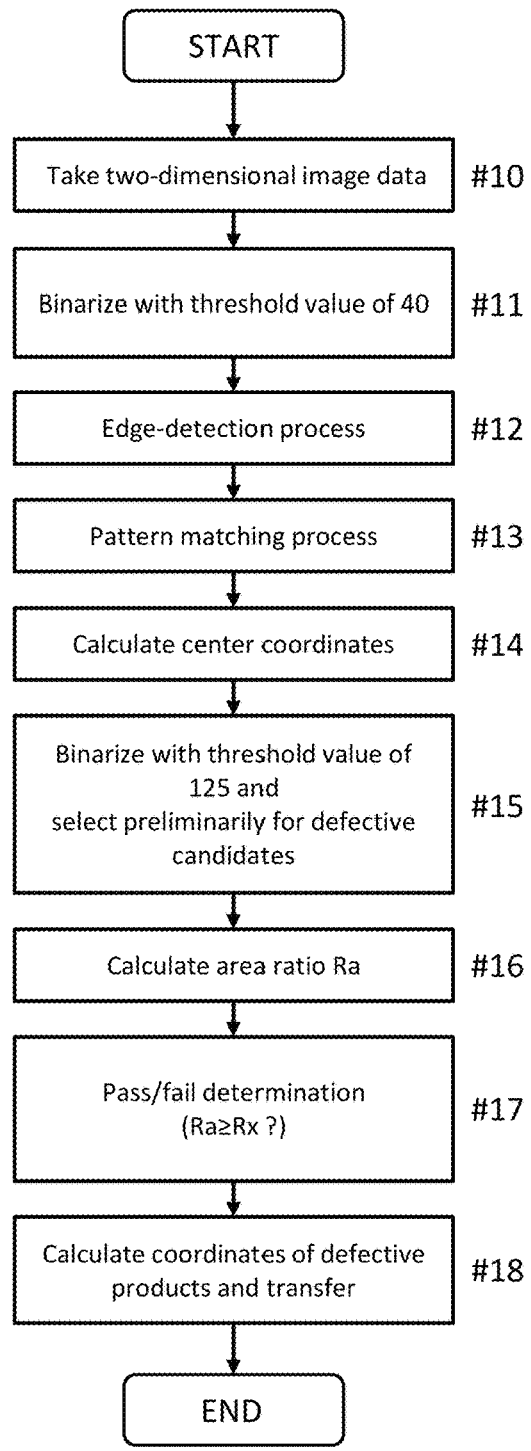
FIG. 10 is a flow chart illustrating a procedure for the first determination process by the determining device.

Next, a procedure for the determination process by the determining device 14 which determines the pass/fail for each object to be sorted 10 based on the two-dimensional image data DA generated by the sensor 13 will be described referring to the flow chart shown in FIG. 10.

The determining device 14 is configured as a computer system including a processor (such as a CPU) and a storage device for storing computer instructions, data, and the like, and the computer instructions stored in the storage device are executed on the processor, so that the determination process described below is performed. In other words, the determining device 14 is configured with well-known computer hardware and computer software including computer instructions for performing the determination process described below. Since the computer hardware and the computer software constituting the determining device 14 are not the subject matter of the present invention, their explanations are omitted.

The determination process starts from Step #10, and in Step #10, the two-dimensional image data DA (2488 pixel× 2055 pixels×8 bits) generated by the sensor 13 is taken into the determining device 14. Subsequently, in Step #11, the two-dimensional image data DA is binarized with a threshold value of 40. This enables the edge-detection process to be performed on all the objects to be sorted 10 regardless of whether they are normal or abnormal. Subsequently, in Step #12, the edge-detection process is performed on the pixels with the gray-scale value of 40 or more of the binarized two-dimensional image data DA.

Subsequently, in Step #13, a pattern matching process is performed on the edge-detected two-dimensional image data DA using matching figures of geometric shapes registered in advance. As a result, the matching figures are assigned to all the objects to be sorted 10 in the inspection region IA respectively. The existence range of the entire shell of the object to be sorted 10 is approximated by the existence range of the matching figure (ellipse). The assigned matching figure (ellipse) is stored in a predetermined storage area for each object to be sorted 10. In the present embodiment, an ellipse is used as the matching figure. Since the pattern matching process of the present embodiment is a process using a well-known pattern matching algorithm, and the details of the process are not the subject matter of the present invention, a detailed description thereof will be omitted. However, to briefly describe the schemata, the pattern matching process in the present embodiment is a process of calculating a score by digitizing the correlation (overlap level, pyramid level, contrast, and the like) between the edge-detected two-dimensional image and the matching figure and of matching the matching figure if the calculated score is within the set allowable range. Note that the pattern matching algorithm used in Step #13 is not limited to the above-described algorithm, and various known algorithms may be used in combination of one or more.

Subsequently, in Step #14, the center coordinates of the matching figures (ellipses) assigned to the respective objects to be sorted 10 by the pattern matching process are calculated and stored in a predetermined storage area for each of the objects to be sorted 10. Unique identification numbers are assigned to the respective objects to be sorted 10 according to the calculated center coordinates, and the center coordinates are stored in association with the identification numbers.

Subsequently, in Step #15, the two-dimensional image data DA taken into the determining device 14 in Step #10 is binarized with a threshold value of 125, and when one or more pixels with a threshold value of 125 or more exist in the matching figures (ellipses) assigned to the respective objects to be sorted 10 in the pattern matching process in Step #13, the objects to be sorted 10 corresponding to such matching figures are preliminarily selected as defective candidates.

Subsequently, in Step #16, for each object to be sorted 10 of the defective candidates preliminarily selected in Step #15, the area of the assigned matching figure (ellipse) is approximately calculated as the area S0 of the entire shell of the object to be sorted 10, the area occupied by the pixel with the gray-scale value of 125 or more in the matching figure of the object to be sorted 10 is approximately calculated as the adhesion area S1 of the BGY fluorescent material, and the area ratio Ra between these two areas S0, S1 (=S1/S0) is calculated, and these calculated results are stored in a predetermined storage area for each of the objects to be sorted 10. Here, since it is sufficient to calculate the areas S0, S1 as relative values for the calculation of the area ratio Ra, in the present embodiment, the area S0 can be calculated as the number of pixels existing in the matching figure, and the area S1 can be calculated as the number of pixels with the gray-scale value of 125 or more existing in the matching figure.

Subsequently, in Step #17, it is determined whether the area ratio Ra calculated for each defective candidate in Step #16 is equal to or larger than a predetermined set value Rx. The object to be sorted 10, which is the defective candidate for which Ra≥Rx is determined, is identified as a defective product. The object to be sorted 10, which is the defective candidate for which Ra<Rx is determined, is not identified as the defective product. After repeatedly executing the pass/fail determination in Step #17 for all the defective candidates, the process proceeds to Step #18.

Subsequently, in Step #18, with respect to the objects to be sorted 10 of all the defective candidates identified as defective products, the coordinate data of the center coordinates of the corresponding matching figures is transferred as the coordinates of the defective products to a remover for removing the object to be sorted 10 identified as a defective product (see the seventh embodiment), and the determination process is terminated.

As another embodiment of Steps #17 and #18, the following steps can be performed. The pass/fail determination of Step #17 is performed for each defective candidate, and only when it is identified as a defective product, the transferring process of Step #18 is continuously performed, and when it is not identified as a defective product, Step #18 is skipped. That is, the processes of Steps #17 and #18 may be repeatedly executed for each defective candidate for the objects to be sorted 10 of all the defective candidates.

In the present embodiment, the set value Rx may be arbitrarily set, for example, within a range of 0.01 to 0.2 in accordance with the condition of the raw material of the object to be sorted 10 and the like. In addition, when the threshold of the binarization process in Step #15 is changed from 125, the set value Rx in Step #17 may be appropriately changed accordingly.

Furthermore, the thresholds of the binarization process in Steps #11 and #15 are not necessarily limited to 40 and 125, and may be appropriately changed in accordance with the above-described adjustments of the light reception sensitivity of the sensor 13, the aperture of lens, and the like, and the ultraviolet illuminance in the inspection region IA.

In the above procedure for the determination process, the defective product is determined based on whether the area ratio Ra between the area S0 of the entire shell of the object to be sorted 10 with the pixel value indicating the fluorescence intensity of 40 or more and the adhesion area S1 of the BGY fluorescent material with the pixel value of 125 or more (=S1/S0) is equal to or larger than a predetermined set value Rx. That is, the object to be sorted with a large adhesion area of the BGY fluorescent material is identified as the defective product.

Figure 11:
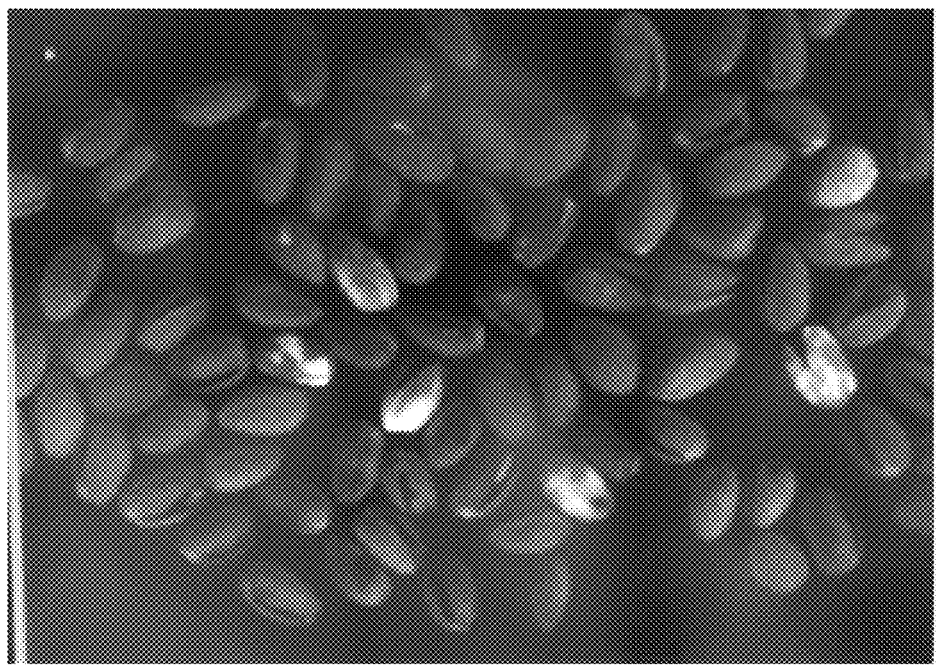
FIG. 11 is a diagram illustrating an exemplary two-dimensional image of the two-dimensional image data DA captured in the determining device 14 in Step #10 of the determination process illustrated in FIG. 10.
Figure 12:
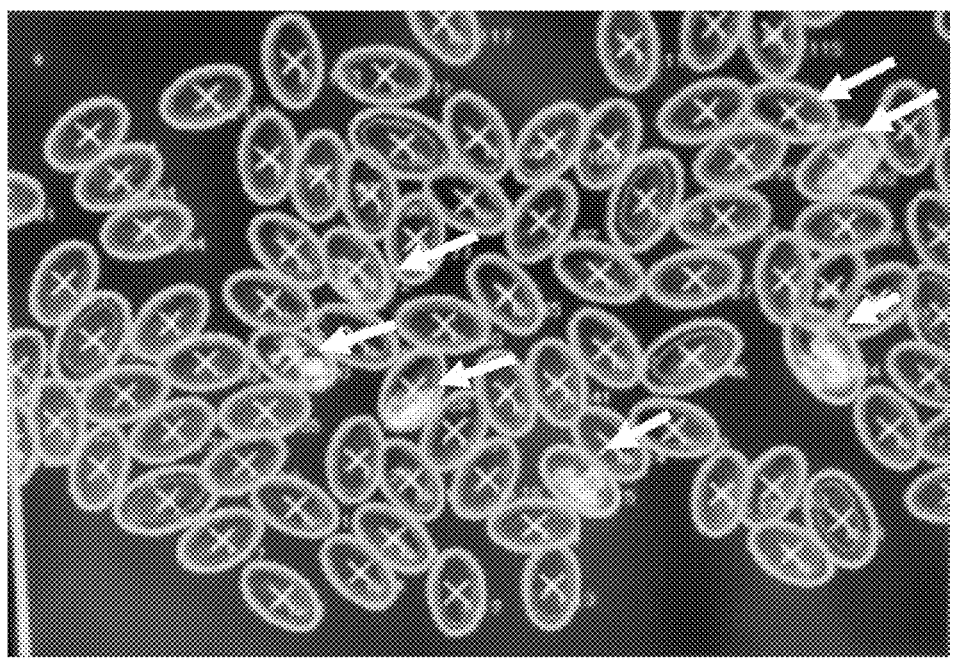
FIG. 12 is a diagram showing matching figures (ellipses) assigned to the two-dimensional image data DA illustrated in FIG. 11 for each object to be sorted in the pattern matching process in Step #13 of the determination process illustrated in FIG. 10, and the centers thereof (indicated by X signs).

FIG. 11 shows two-dimensional images of the two-dimensional image data DA taken into the determining device 14 in Step #10 of the determination process, and FIG. 12 shows the matching figures (ellipses) and centers thereof (indicated by X signs) assigned to the respective objects to be sorted 10 in the pattern matching process in Step #13 of the determination process. The arrows in FIG. 12 indicate the objects to be sorted 10 identified as the defective products in Step #17 of the determination process. It can be seen from FIGS. 11 and 12 that, by executing the determination process illustrated in the flow chart of FIG. 10, the pass/fail determination can be performed simultaneously for a lot of objects to be sorted 10 placed in the inspection region IA on the conveyor belt CB. That is, a high-speed sorting process can be performed for a lot of objects to be sorted 10.

Next, three modifications (the second to fourth procedures for the determination process) of the procedure for the determination process by the determining device 14 (the first procedure for the determination process) described with reference to the flow chart shown in FIG. 10 will be described in the following second to fourth embodiments. The description that overlaps with the first procedure for the determination process is appropriately omitted as necessary. In addition, in the second to fourth embodiments, the configuration of the present sorting device 1 is the same as that described in the first embodiment except for the determination process by the determining device 14, and redundant explanation will be omitted.

Second Embodiment

Figure 13:
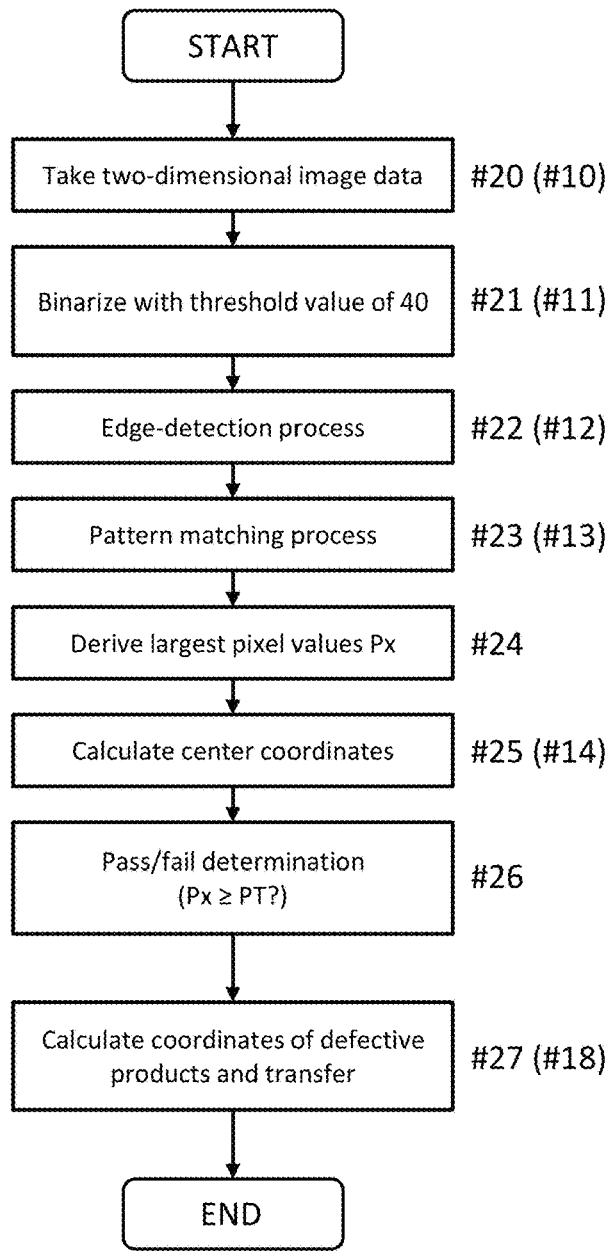
FIG. 13 is a flow chart illustrating a procedure for the second determination process by the determining device.

The first modification (the second procedure for the determination process) of the procedure for the determination process by the determining device 14 will be described referring to the flow chart shown in FIG. 13. In FIG. 13, when the processing content of the step of the second procedure for the determination process is the same as the processing content of the step of the first procedure for the determination process, the step number of the first procedure for the determination process is added in parentheses on the right side of the step number.

The determination process starts in Step #20, and in Step #20, the two-dimensional image data DA (2488 pixels×2055 pixels×8 bits) generated by the sensor 13 is taken into the determining device 14. Subsequently, in Step #21, the two-dimensional image data DA is binarized with a threshold value of 40. Subsequently, in Step #22, the edge-detection process is performed on the pixels with the gray-scale value of 40 or more of the binarized two-dimensional image data DA.

Subsequently, in Step #23, a pattern matching process is performed on the edge-detected two-dimensional image data DA using matching figures of geometric shapes registered in advance. Thus, the existence range of the entire shell of the object to be sorted 10 is approximated by the existence range of the matching figure (ellipse). Steps #20 to #23 are the same as Steps #10 to #13 of the first procedure for the determination process.

Subsequently, in Step #24, the largest pixel values (gray-scale values) Px of the pixels existing in the matching figures (ellipses) assigned to the respective objects to be sorted 10 by the pattern matching process are derived for each of the objects to be sorted 10 and stored in a predetermined storage area.

Subsequently, in Step #25, the center coordinates of the matching figures (ellipses) assigned to the respective objects to be sorted 10 by the pattern matching process are calculated and are stored in a predetermined storage area for each of the objects to be sorted 10. Unique identification numbers are assigned to the respective objects to be sorted 10 according to the calculated center coordinates, and the center coordinates are stored in association with the identification numbers. Step #25 is the same as Step #14 of the first procedure for the determination process. Step #24 may be performed after Step #25 or in parallel with Step #25.

Subsequently, in Step #26, it is determined whether the largest pixel value Px derived for each object to be sorted 10 in Step #24 is equal to or larger than a predetermined threshold Pt. The object to be sorted 10, for which Px≥Pt is determined, is identified as the defective product. The object to be sorted 10, for which Px<Pt is determined, is not identified as the defective product. After repeatedly executing the pass/fail determination in Step #26 for all the defective candidates, the process proceeds to Step #27.

Subsequently, in Step #27, for all the objects to be sorted 10 identified as the defective product, the coordinate data of the center coordinates of the corresponding matching figures is transferred as the coordinates of the defective products to a remover for removing the object to be sorted 10 identified as the defective product (see the seventh embodiment), and the determination process is terminated.

As another embodiment of Steps #26 and #27, similarly to another embodiment of Steps #17 and #18 of the first procedure for the determination process, the pass/fail determination of Step #26 is performed for each object to be sorted 10, and only when it is identified as a defective product, the transfer processing of Step #27 is continuously performed, and when it is not identified as a defective product, Step #27 is skipped. That is, the processes of Steps #26 and #27 may be repeatedly executed for each of all the objects to be sorted 10.

In the present embodiment, the threshold Pt may be arbitrarily set, for example, within a range of 125 to 200 in accordance with the condition of the raw material of the object to be sorted 10 and the like.

In the first procedure for the determination process, based on whether the area ratio Ra (=S1/S0 between the area S0 of the entire shell of the object to be sorted 10 and the adhesion area S1 of the BGY fluorescent material is equal to or larger than a predetermined set value Rx, the object to be sorted with a large adhesion area of the BGY fluorescent material is identified as the defective product. On the other hand, in the second procedure for the determination process (first modification), based on whether the maximum value Px of the fluorescence intensities indicated by the respective pixel values within the entire shell of the object to be sorted 10 is equal to or larger than a predetermined threshold Pt, the object to be sorted with a large fluorescence intensity of the BGY fluorescent material is identified as the defective product. Therefore, the first and second procedures for the determination process are different in the above determination bases.

As another embodiment of Steps #24 and #26, Step #24 is omitted, and in Step #26, it is determined whether one or more pixels with pixel value (gray-scale value) equal to or larger than a predetermined threshold Pt exist among the plurality of pixels existing in the matching figure (ellipse) assigned to each object to be sorted 10 by the pattern matching process. When one or more pixels with a pixel value equal to or larger than the predetermined threshold Pt exist, the largest pixel value (gray-scale value) Px derived when Step #24 is executed is always equal to or larger than the predetermined threshold Pt.

Third Embodiment

Figure 14:
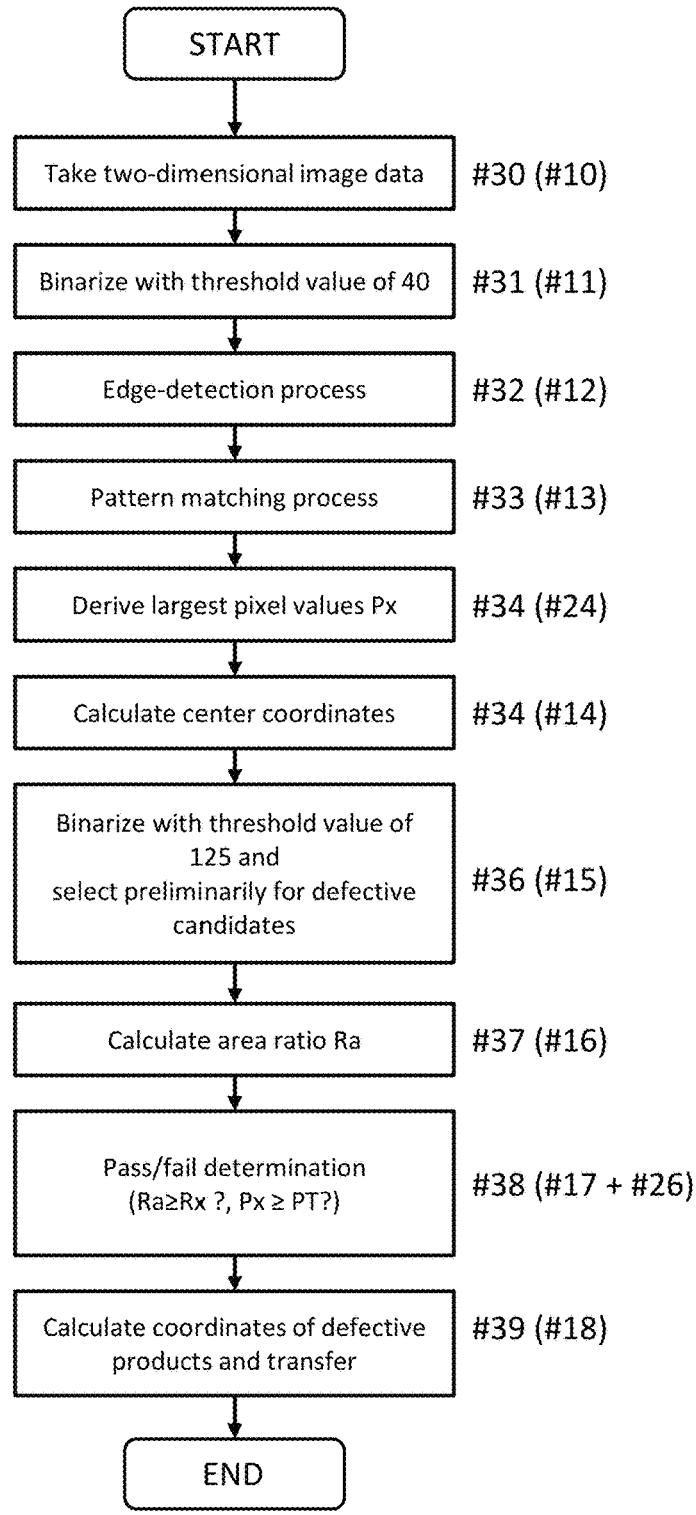
FIG. 14 is a flow chart illustrating a procedure for the third determination process by the determining device.

The second modification (the third procedure for the determination process) of the procedure for the determination process by the determining device 14 will be described referring to the flow chart shown in FIG. 14. In FIG. 14, when the processing content of the step of the third procedure for the determination process is the same as the processing content of the step of the first or second procedure for the determination process, the step number in the first or second procedure for the determination process is added in parentheses on the right side of the step number.

The determination process starts in Step #30, and in Step #30, the two-dimensional image data DA (2488 pixels×2055 pixels×8 bits) generated by the sensor 13 is taken into the determining device 14. Subsequently, in Step #31, the two-dimensional image data DA is binarized with a threshold value of 40. Subsequently, in Step #32, the edge-detection process is performed on the pixels with the gray-scale value of 40 or more of the binarized two-dimensional image data DA.

Subsequently, in Step #33, a pattern matching process is performed on the edge-detected two-dimensional image data DA using matching figures of geometric shapes registered in advance. Thus, the existence range of the entire shell of the object to be sorted 10 is approximated by the existence range of the matching figure (ellipse). Steps #30 to #33 are the same as Steps #10 to #13 of the first procedure for the determination process.

Subsequently, in Step #34, the largest pixel values (gray-scale values) Px of the pixels existing in the matching figures (ellipses) assigned to the respective objects to be sorted 10 by the pattern matching process are derived for each of the objects to be sorted 10 and stored in a predetermined storage area. Step #34 is the same as Step #24 of the second procedure for the determination process.

Subsequently, in Step #35, the center coordinates of the matching figures (ellipses) assigned to the respective objects to be sorted 10 by the pattern matching process are calculated and are stored in a predetermined storage area for each of the objects to be sorted 10. Unique identification numbers are assigned to the respective objects to be sorted 10 according to the calculated center coordinates, and the center coordinates are stored in association with the identification numbers. Step #34 may be performed after Step #35 or in parallel with Step #35.

Subsequently, in Step #36, the two-dimensional image data DA taken into determining device 14 in Step #30 is binarized with a threshold value of 125, and when one or more pixels with a threshold value of 125 or more exist in the matching figures (ellipses) assigned to the respective objects to be sorted 10 in the pattern matching process in Step #33, the objects to be sorted 10 corresponding to such matching figures are preliminarily selected as defective candidates.

Subsequently, in Step #37, for each object to be sorted 10 of the defective candidates preliminarily selected in Step #36, the area of the assigned matching figure (ellipse) is approximately calculated as the area S0 of the entire shell of the object to be sorted 10, the area occupied by the pixel with the gray-scale value of 125 or more in the matching figure of the object to be sorted 10 is approximately calculated as the adhesion area S1 of the BGY fluorescent material, and the area ratio Ra between these two area S0,S1 (=S1/S0) is calculated and these calculated results are stored in a predetermined storage area. Steps #35 to #37 are the same as Steps #14 to #16 of the first procedure for the determination process.

Subsequently, in Step #38, it is determined whether the largest pixel value Px derived for each object to be sorted 10 in Step #34 is equal to or larger than a predetermined threshold Pt, and it is determined whether the area ratio Ra calculated for each defective candidate in Step #37 is equal to or larger than a predetermined set value Rx. The objects to be sorted 10 of all the defective candidates, for which Px≥Pt and Ra≥Rx are determined, are identified as the defective products. The object to be sorted 10, for which Px<Pt or Ra<Rx is determined, is not identified as the defective product. After repeatedly executing the two types of pass/fail determination in Step #38 for all the objects to be sorted 10 and the defective candidates, the process proceeds to Step #39. Step #38 is a process content obtained by combining Step #17 of the first procedure for the determination process and Step #26 of the second procedure for the determination process.

Subsequently, in Step #39, for the objects to be sorted 10 of all the defective candidates identified as the defective products, the coordinate data of the center coordinates of the corresponding matching figures is transferred as the coordinates of the defective products to a remover for removing the object to be sorted 10 identified as the defective product (see the seventh embodiment), and the determination process is terminated.

As another embodiment of Steps #38 and #39, similarly to another embodiment of Steps #17 and #18 of the first procedure for the determination process, the two types of pass/fail determination of Step #38 are performed for each of the objects to be sorted 10 and each of the defective candidates, and only when it is identified as a defective product, the transfer processing of Step #39 is continuously performed, and when it is not identified as a defective product, Step #39 is skipped. That is, the processes of Steps #38 and #39 may be repeatedly executed to all the objects to be sorted 10, for each object to be sorted 10 and for each defective candidate.

The third procedure for the determination process is a processing procedure in which the first and second procedures for the determination process are integrated.

As a modification of the third determination process, in Step #38, the objects to be sorted 10 of all the defective candidates, for which Px≥Pt or Ra≥Rx is determined, are identified as the defective products, and all the objects to be sorted 10, for which Px<Pt and Ra<Rx are determined, are not identified as the defective products. However, in this modification, since it is easily identified as a defective product, the threshold Pt and the set value Rx may be set higher than in the third determination process.

As another embodiment of Steps #34 and #38, similar to another embodiment of Steps #24 and #26 of the second procedure for the determination process described above, Step #34 is omitted, and in Step #38, it is determined whether one or more pixels with pixel values (gray-scale values) equal to or greater than a predetermined threshold Pt exist in a plurality of pixels existing in the matching figure (ellipse) assigned to each object to be sorted 10 by the pattern matching process.

Fourth Embodiment

Figure 15:
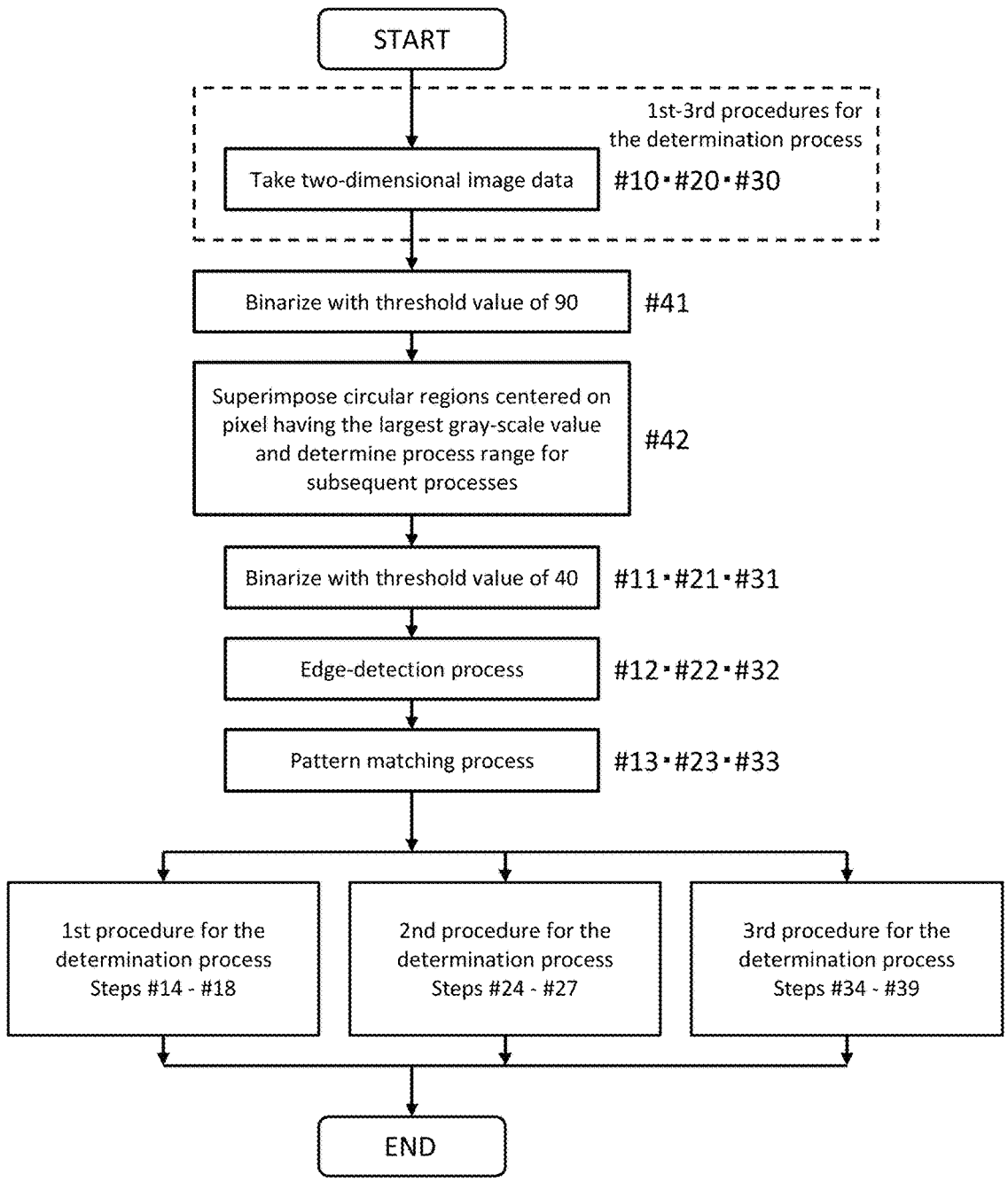
FIG. 15 is a flow chart illustrating a procedure for the fourth determination process by the determining device.

The third modification (the fourth procedure for the determination process) of the procedure for the determination process by the determining device 14 will be described referring to the flow chart shown in FIG. 15.

The fourth procedure for the determination process is a common modification to the above-described first to third procedures for the determination process. In the first to third procedures for the determination process, at Steps #13, #23, and #33, the pattern matching process is performed on the edge-detected two-dimensional image data DA. Here, since the edge-detection process targets the two-dimensional image data DA binarized with a threshold value of 40, all the objects to be sorted 10 are included in the edge-detected two-dimensional image. If the total number of the objects to be sorted 10 disposed in the inspection region IA is 100, the pattern matching process is performed for the 100 objects to be sorted 10.

On the other hand, in the fourth procedure for the determination process described below, it is an object to significantly reduce the time and load required for the pattern matching process, when there are a large number of objects to be sorted 10 and the defective product rate is low, by excluding a range in which the object to be sorted 10 that can be identified as a defective product cannot exist from a processing range of the pattern matching processing in advance to greatly reduce the processing range compared with the processing ranges of the first to third procedures for the determination process.

Therefore, in the fourth procedure for the determination process, before the pattern matching process of the first to third procedures for the determination process (Steps #13, #23, and #33) and its preparatory process (the binarization process with a threshold value of 40 and the edge-detection process (Steps #11 and #12, #21 and #22, #31 and #32)), a pre-process for determining a processing range of the pattern matching process and its preparatory process is executed. The pre-process will be described below.

The pre-process of the fourth procedure for the determination process is performed between the process for taking the two-dimensional image data DA in the first to third procedures for the determination process (Steps #10, #20, and #30) and the preparatory process of the pattern matching process (Steps #11, #21, and #31).

The pre-process of the fourth determination processing starts from Step #41, and in Step #41, the two-dimensional image data DA is binarized with a threshold value of 90. The range binarized with the threshold value of 90 is narrower than the range subjected to the edge-detection process after the preparatory process of the first to third procedures for the determination process. Therefore, if the pattern matching process of the first to third procedures for the determination process (Steps #13, #23, and #33) is performed, groups of pixels constituting parts of the respective objects to be sorted 10 with a gray-scale value of 90 or more binarized with a threshold value of 90 exist dispersedly inside the matching figures assigned respectively to all the objects to be sorted 10 in the inspection region IA.

Subsequently, in Step #42, a pixel having the largest gray-scale value in each group of pixels constituting a part of each object to be sorted 10 is specified for each pixel group, a circular region centered on the pixel having the largest gray-scale value is set with a diameter 45 mm, for example, for each pixel group, and the circular region for each group of pixels is superimposed to each other to determine the process range of the pattern matching process and its preparatory process.

Subsequently, the process proceeds to any one of Steps #11, #21, and #31 of the first to third procedures for the determination process according to which one of the first to third procedures for the determination process is to be performed. Since the processing contents after the process proceeded have already been described in the first to third procedures for the determination process, the redundant descriptions will be omitted. The reason why the process proceeds to the binarization process with a threshold value of 40 in Steps #11, #21, and #31 of the first to third procedures for the determination process is that pixels with the threshold value less than 40 may be included in each circular region of the processing range.

The size of the in-shell pistachio is about 20 mm in length of the major axis, and the object to be sorted 10 can be accommodated in the circular region with a diameter 45 mm centered on the pixel with the highest BGY fluorescence intensity, even if the BGY fluorescent material of the object to be sorted 10 to be identified as the defective product is located around the shell. The diameter defining the circular region is not limited to 45 mm and may be arbitrarily set in accordance with to the condition of the raw material of the object to be sorted 10 and the like.

The threshold value for the binarization process in Step #41 is not limited to 90 and can be arbitrarily set within the range of 60 to 120, for example, and can be changed in accordance with the condition of the raw material of the object to be sorted 10 and the like.

Depending on the condition of the raw material, the number of the circular regions set in Step #42 is at most about 10 in the inspection region IA of the two-dimensional image data DA, and the processing range determined in Step #42 is as small as about 15% in area ratio with respect to the inspection region IA. Consequently, the number of the objects to be sorted 10 to be subjected to the pattern matching process performed in the first to third procedures for the determination process can be reduced to about one tenth, and the calculation time required for the pattern matching process can also be reduced to about one tenth.

Fifth Embodiment

Figure 16:
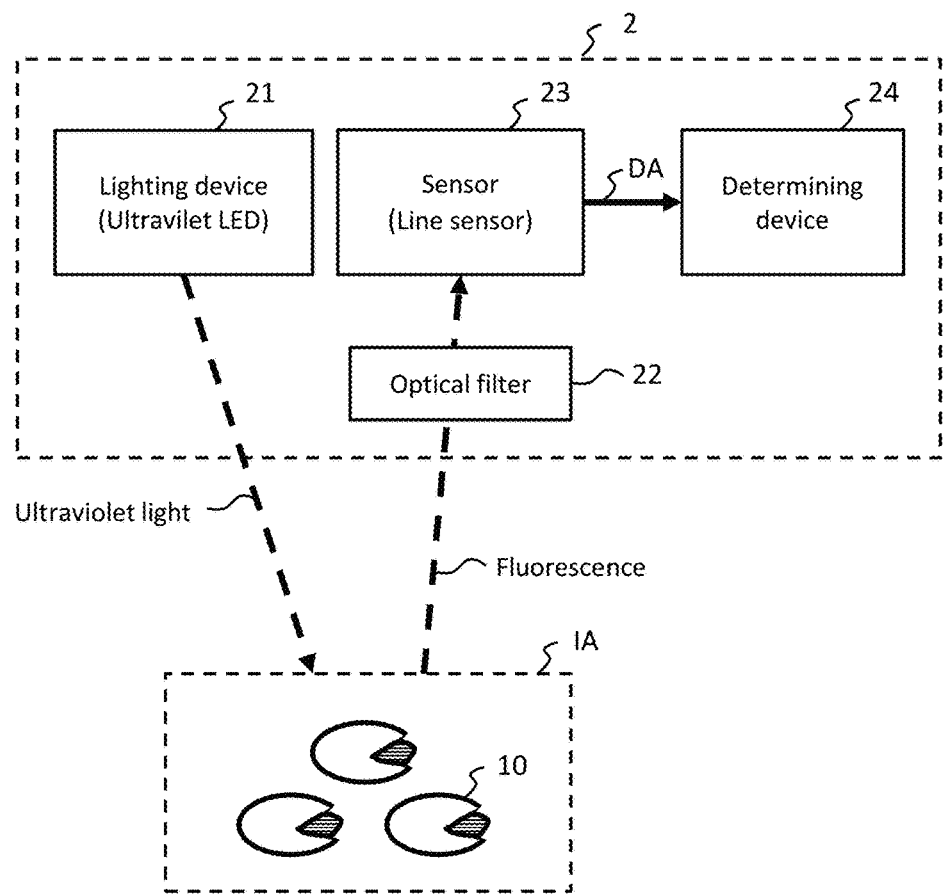
FIG. 16 is a diagram illustrating an exemplary configuration of the pistachio sorting device according to the fifth embodiment.

As shown in FIG. 16, the present sorting device 2 of the fifth embodiment comprises a lighting device 21 for irradiating one or more in-shell pistachios which are one or more objects to be sorted 10 disposed in an inspection region IA with ultraviolet light, an optical filter 22 for selectively transmitting light within a predetermined wavelength range of fluorescence excited by the ultraviolet light irradiated from the lighting device 21 and emitted from the objects to be sorted 10, a sensor 23 for repeatedly detecting multiple times an one-dimensional intensity distribution of the fluorescence transmitted through the optical filter 22 to generate two-dimensional image data DA indicating a two-dimensional intensity distribution of fluorescence in the inspection region IA, and a determining device for determining a pass/fail for each object to be sorted 10 based on the two-dimensional image data DA.

In the first embodiment, the sensor 13 constituting the present sorting device 1 is composed of the area camera, but in the fifth embodiment, the sensor 23 is composed of a line sensor.

In the present embodiment, instead of the monochrome CCD camera having 5 M pixels (2488 pixels in the horizontal direction×2055 pixels in the vertical direction) used in the first embodiment, a line sensor having 7500 pixels in the horizontal direction, which is three times the number of pixels in the horizontal direction, is used. In this instance, since the horizontal direction of line sensor is the width direction of the conveyor belt CB (orthogonal to the traveling direction of the conveyor belt CB), the width of the conveyor belt CB can be expanded to three times (e.g., 1800 mm) the width of the conveyor belt CB used in the first embodiment (e.g., 600 mm), and the inspection throughput is increased to three times (e.g., 1800 kg/hour).

In the first embodiment using an area camera as the sensor 13, the frame vertical direction of the two-dimensional image data DA generated by the area camera is parallel to the traveling direction of the conveyor belt CB. On the other hand, in the fifth embodiment in which the sensor 23 is the line sensor, the distance traveled for a certain period of the conveyor belt CB corresponds to the frame vertical direction of the two-dimensional image data DA generated by the sensor 23. In this case, the moving speed of the conveyor belt CB is read by an encoder attached to the belt conveyor, and the optimum acquisition time is set so that the length of the frame vertical direction becomes a predetermined value.

For example, in order to set the number of pixels in the vertical direction to 2055, scanning by the line sensor is repeated 2055 times to generate the two-dimensional image data DA of 7500 pixels×2055 pixels. For example, when image acquisition is performed for a movement of 400 mm of the conveyor belt CB, 2055 scans are performed in about 4 seconds to generate the two-dimensional image data DA. An encoder is required to constantly monitor the moving speed of the conveyor belt CB, and the number of scans needs to be optimized based on the moving speed obtained from the encoder.

In the present embodiment, as in the first embodiment, the lighting device 21 is composed of an ultraviolet LED in which the maximum peak wavelength is within a range of 345 nm to 390 nm, more preferably 350 nm to 375 nm. In addition, each lighting device 21 is provided with an optical filter which blocks a wavelength component of 400 nm or more emitted from the ultraviolet LED.

In the present embodiment, since the lighting device 21 only needs to irradiate the area scanned by the line sensor (scanning area) in the inspection region IA, the irradiation area in the vertical direction can be narrowed, but since the width of the conveyor belt CB is enlarged by three times, the irradiation area in the horizontal direction is enlarged. Thus, three of the lighting devices 21 with 12 high-power ultraviolet LEDs are used to illuminate the liner scanning area with a total of 36 high-power ultraviolet LEDs.

In the present embodiment, the line sensor having a large number of pixels is used as the sensor 23, so that there are merits such as an increase in the inspection throughput due to an increase in the width of the conveyor belt CB and a reduction in the ultraviolet illumination area of the lighting device 21 in the traveling direction of the conveyor belt CB.

As in the first embodiment, the optical filter 22 is configured to selectively transmit lights in a wavelength range of 500 nm to 600 nm. However, as in the first embodiment, since the optical filter 22 is attached in front of the light receiving opening of the sensor 23, the size of the optical filter 22 is adjusted to align with the size of the opening of the light-receiving surface of the line sensor.

In the present embodiment, as in the first embodiment, the lighting device 21, the optical filter 22, and the sensor 23 are installed in a lightproof box (not shown), and the entry of ambient light into the inspection region IA is blocked. In addition, under the conditions described in the first embodiment, the lighting device 21, the optical filter 22, and the sensor 23 do not necessarily need to be installed in the lightproof box.

The procedure for the determination process of the determining device 24 differs only in the number of pixels of the two-dimensional image data DA to be processed, and the procedure for the determination process is the same as any one of the first to fourth procedures for the determination process described in the first to fourth embodiments, and therefore redundant explanation will be omitted.

Sixth Embodiment

In the fifth embodiment, the lighting device 21 and the sensor 23 constituting the present sorting device 2 are configured by ultraviolet LEDs and a line sensor, but in the sixth embodiment, the lighting device 31 constituting the present sorting device 3 comprises an ultraviolet semiconductor laser as a light source, and the emission wavelength thereof is set to be the same as the maximum peak wavelength of the lighting devices 11 and 21 described in the first and fifth embodiments.

Figure 17:
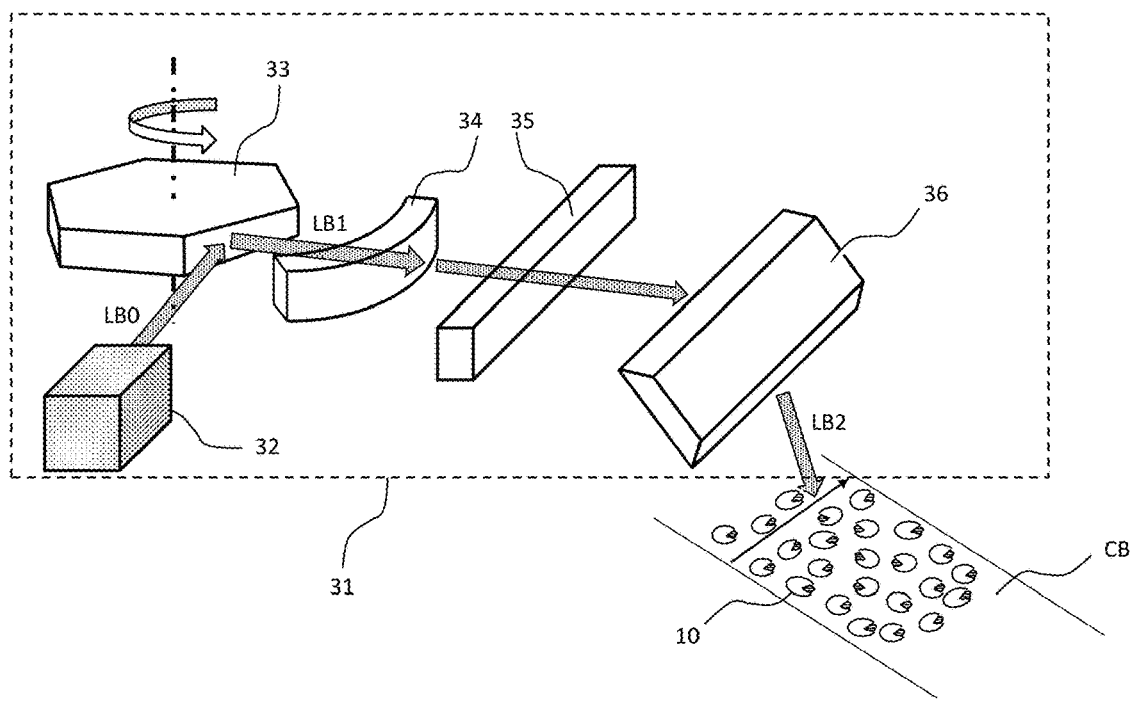
FIG. 17 is a diagram schematically illustrating an exemplary configuration of the lighting device of the pistachio sorting device according to the sixth embodiment.

The sixth embodiment is different from the fifth embodiment in that the lighting device 31 is composed of the ultraviolet semiconductor laser, and the remaining components (the optical filter 22, the sensor 23, the determining device 24, and the like) are the same as those of the fifth embodiment, and redundant explanation will be omitted. Therefore, the exemplary configuration of the present sorting device 2 of the fifth embodiment shown in FIG. 16 becomes the exemplary configuration of the present sorting device 3 of the sixth embodiment, if the lighting device 21 is replaced with the lighting device 31 described below. Referring to FIG. 17, the lighting device 31 will be described below.

As illustrated in FIG. 17, the lighting device 31 includes an optical system including the ultraviolet semiconductor laser 32 as the light source, a polygon mirror 33, Fθ lenses 34, 35, and a reflecting mirror 36. The beam-shaped laser light LB0 emitted from the semiconductor laser 32 is irradiated onto the polygon mirror 33 rotating at a high speed. The laser light LB1 reflected by the polygon mirror 33 is converged by the Fθ lenses 34, 35 and irradiated onto the reflecting mirror 36. The laser light LB2 reflected by the reflecting mirror 36 is scanned at high speed in the width direction on the conveyor belt CB. While the laser light LB0 traverses one surface of the polygon mirror 33, the laser light LB2 finishes scanning one line on the conveyor belt CB. The Fθ lenses are arranged so that the laser light LB2 irradiated on the conveyor belt CB by the line sensor of the sensor 23 is within the angle of view. The speed of the laser light LB2 scanning the conveyor belt CB and the scanning speed of the line sensor are synchronized by adjusting the rotation speed of the polygon mirror 33.

Since the polygon mirror 33, the Fθ lenses 34, 35, and the reflecting mirror 36 are well-known optical components commonly used in optical systems for scanning laser light on a predetermined focal plane, explanations about the individual optical components will be omitted.

Seventh Embodiment

Figure 18:
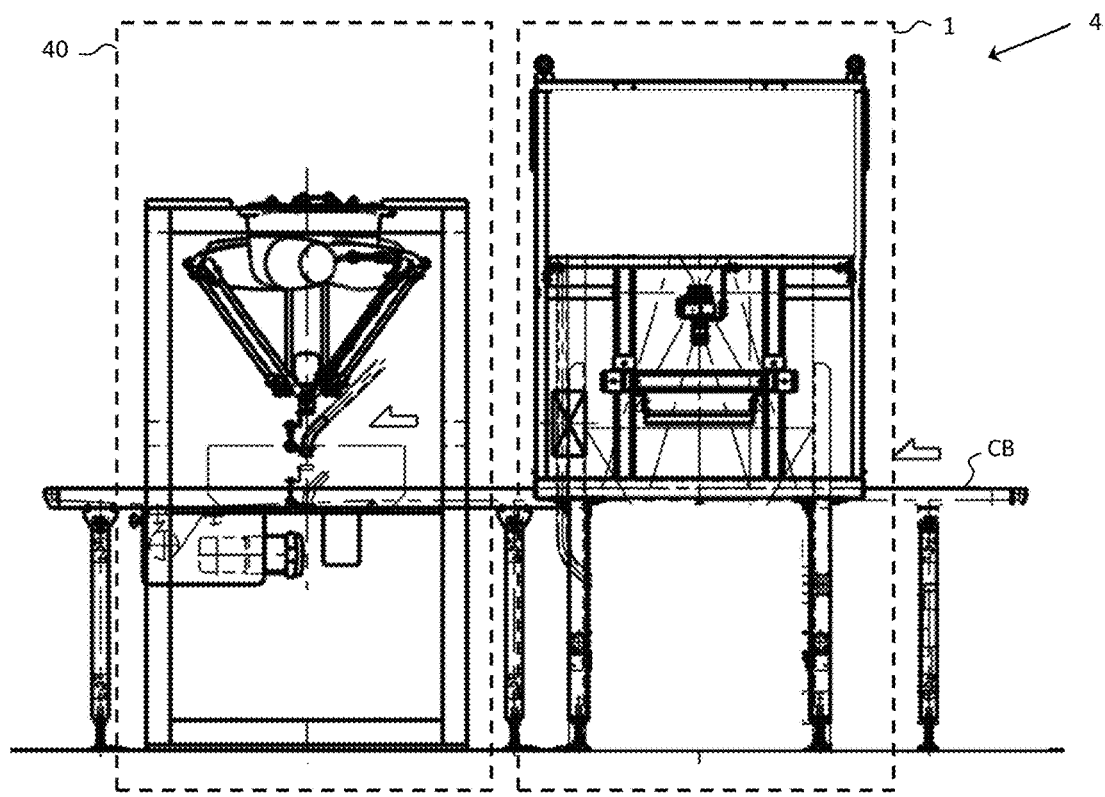
FIG. 18 is an explanatory diagram illustrating an exemplary configuration of the pistachio sorting device according to the seventh embodiment.

As shown in FIG. 18, the present sorting device 4 of the seventh embodiment is configured by adding a remover 40 that physically removes the object to be sorted 10 identified as a defective product by the determining device 14 to the present sorting device 1 described in the first to fourth embodiments. Since the present sorting device 1 has already been described in detail in the first to fourth embodiments, a redundant description thereof will be omitted. Hereinafter, the remover 40 will be described.

In the present embodiment, the remover 40 is configured with a parallel link robot. A suction hose having a shutter mechanism is attached to a pickup portion of the parallel link robot. The conveyor belt CB is provided across the present sorting device 1 and the remover 40, and the belt surface of the conveyor belt CB moves from the present sorting device 1 toward the remover 40. That is, the present sorting device 1 is disposed upstream of the conveyor belt CB, and the remover 40 is disposed downstream thereof. The belt conveyor is provided with an encoder for constantly monitoring the moving speed of the conveyor belt CB.

The coordinate data of the center coordinates of the matching figures (ellipse) of all the objects to be sorted 10 identified as the defective products in the determining device 14 of the present sorting device 1 (the coordinates of the defective products) is transferred from the determining device 14 to the parallel link robot. The coordinate data transferred from the determining device 14 is converted into position coordinates of the objects to be sorted 10 corresponding to the respective coordinate data within a movable range of the parallel link robot when the objects to be sorted 10 reach the movable range based on the moving speed of the conveyor belt CB obtained from the encoder.

The center of the pickup unit is moved to be directly above the converted position coordinate, and the shutter of the pickup unit stops at a position 10 mm above the conveyor belt CB, and at the same time the shutter opens. The inside of the shutter is decompressed, and a piece of the in-shell pistachio of the object to be sorted 10 identified as the defective product is sucked, and the shutter is closed, whereby the object to be sorted 10 identified as the defective product is selected and removed. In the present embodiment, sorting and removal by the parallel link robot eliminates overshoot and vibration, enabling highly reliable picking.

Figure 19:
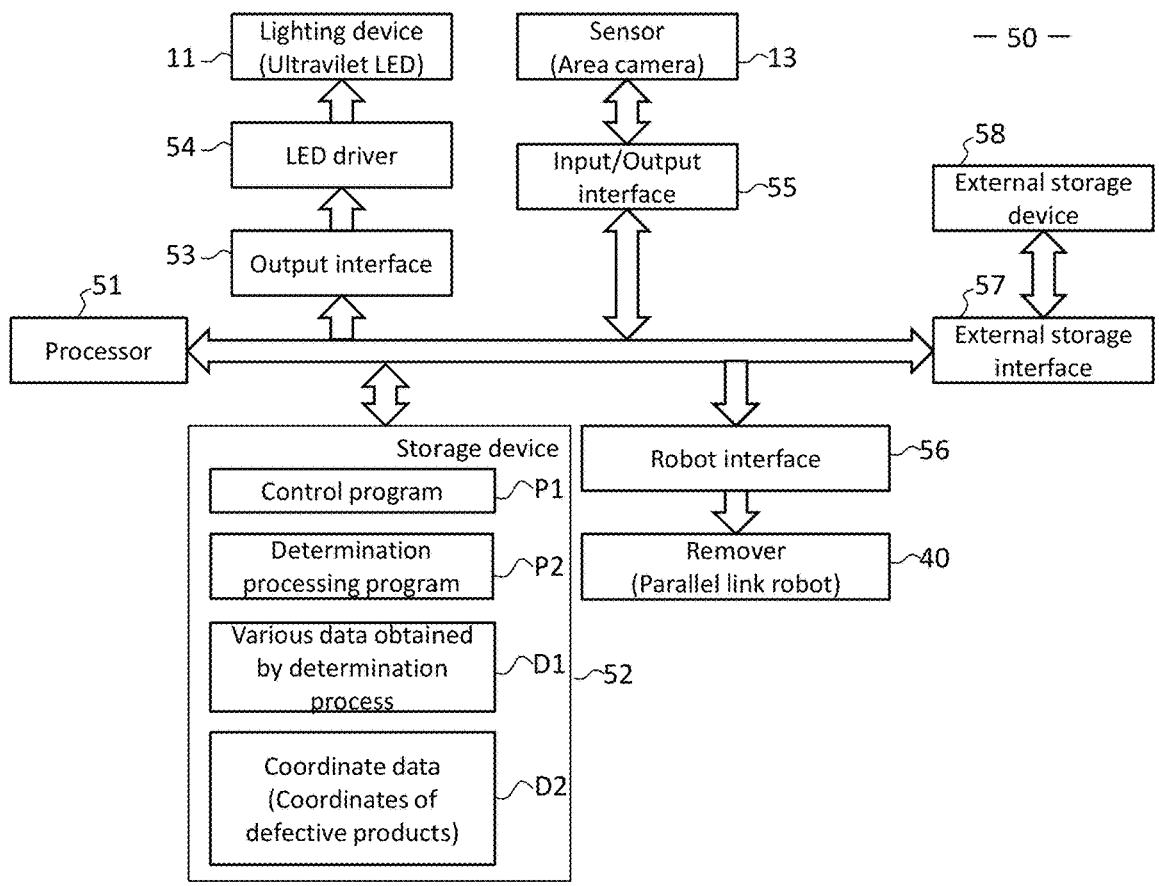
FIG. 19 is an explanatory diagram illustrating an exemplary system configuration for the pistachio sorting device according to the seventh embodiment.

FIG. 19 shows a system configuration of the present sorting device 4 of the present embodiment. The system 50 of the present sorting device 4 is configured with a processor 51, a storage device 52, an output interface 53, an LED driver 54, the lighting device 11 (ultraviolet LEDs), an input/output interface 55, the sensor 13 (area camera), a robot interface 56, the remover 40 (parallel link robot), an external storage interface 57, and an external storage device 58.

The storage device 52 stores a control program P1 for controlling the entire system 50, a determination processing program P2 for defining a procedure for the determination process by the determining device 14, a various data D1 obtained by the procedure for the determination process (the two-dimensional image data DA, an event of detecting the defective products, etc.), and the coordinate data D2 of the center coordinates of the matching figures (ellipse) of all the objects to be sorted 10 identified as the defective products obtained in the procedure for the determination process (the coordinates of the defective products).

Based on the control program P1, the lighting device 11 is operated, and the two-dimensional image data DA of the objects to be sorted 10 in the inspection region IA is taken into the storage device 52 from the sensor 13. Based on the determination processing program P2, the first to fourth procedures for the determination process described in the first to fourth embodiments are performed to the two-dimensional image data DA taken into the storage device 52, and the coordinate data D2 of the center coordinates of all the objects to be sorted 10 identified as the defective products are transferred to the remover 40 (parallel link robot). The moving distance of the conveyor belt CB is calculated based on the moving speed of the conveyor belt CB obtained from the encoder, and the moving distance is adjusted with respect to the coordinate data D2 of the center coordinates, and the center coordinates in the coordinate data D2 are converted into the position coordinate within the movable range of the parallel link robot when reaching the movable range. Consequently, the object to be sorted 10 that has reached the converted position coordinate is removed by the pickup unit of the parallel link robot.

The system configuration of the present sorting device 4 shown in FIG. 19 can be used as the system configuration of the present sorting device 1 of the first to fourth embodiments, the present sorting device 2 of the fifth embodiment, and the present sorting device 3 of the sixth embodiment, except for the robot interface 56 and the remover 40 (parallel link robot).

Other Embodiments (1) The procedure for the determination process by the determining device 14 are not necessarily limited to the first and fourth procedures for the determination process described in the first to fourth embodiments. Various modifications to the procedure for the determination process are possible.

For example, the preliminary selection of the defective candidates in Steps #15 and #36 of the first and third procedures for the determination process may be omitted. In this case, since the adhesion area S1 of the BGY fluorescent material of the object to be sorted 10, which was not a defective candidate, is 0, the area ratio Ra (=S1/S0) is 0 without having to calculate the area S0 of the entire shell. Therefore, when the adhesion area S1 is first calculated for each object to be sorted 10 first and S1=0, the area S0 of the entire shell is not calculated and Ra=0.

Furthermore, in the third procedure for the determination process described in the third embodiment, since the defective candidates are preliminarily selected by the binarization process with the threshold value of 125 in Step #36, the derivation of the largest pixel values (gray-scale values) Px in Step #34 and/or the calculation of the center coordinates in Step #35 may be performed for the defective candidates that have been preliminarily selected after Step #36. When the derivation of the largest pixel values (gray-scale values) Px in Step #34 is performed to the defective candidates that have been preliminarily selected, the determination process in Step #38 is also performed for the defective candidates that have been preliminarily selected.

Furthermore, in the first procedure for the determination process, since the preliminary selection of the defective candidates is performed by the binarization process with the threshold value of 125 in Step #15, the calculation of the center coordinates in Step #14 may be performed for the defective candidates that have been preliminarily selected after Step #15.

Furthermore, in the above-described first to fourth procedures for the determination process, at Steps #13, #23, and #33, the pattern matching process is performed on the edge-detected two-dimensional image data DA. However, even if the matching figure (ellipse) is not assigned to each object to be sorted 10 by the pattern matching process, it is possible to calculate the center coordinates of each object to be sorted 10, the area S0 of the entire shell of each object to be sorted 10, the adhesion area S1 of the BGY fluorescent material adhered to each object to be sorted 10, and the existence range of the entire shell of each object to be sorted 10.

For example, when a plurality of the objects to be sorted 10 is placed on the conveyor belt CB, if the objects to be sorted 10 can be placed so as not to be in contact with each other, for example, since each object to be sorted 10 can be edge-detected in the edge-detection process of Step #12 of the first procedure for the determination process, the center coordinate of each object to be sorted 10, the area S0 of the entire shell of each object to be sorted 10, the adhesion area S1 of the BGY fluorescent material adhered to each object to be sorted 10, and the existence range of the entire shell of each object to be sorted 10 can be easily calculated for each edge-detected region without performing the pattern matching process.

Furthermore, even if the plurality of the objects to be sorted 10 are in contact with each other, for example, the area divided according to the objects to be sorted 10 can be defined as the existence range of the entire shell of each object to be sorted 10, for example, by retracting the edge subjected to the edge-detection process in Step #12 of the first determination process inward by several millimeters once, separating the area surrounded by the edge according to the objects to be sorted 10, and then expanding the retracted edge outward by the amount of retraction. Thus, without performing the pattern matching process, the center coordinate of each object to be sorted 10, the area S0 of the entire shell of each object to be sorted 10, and the adhesion area S1 of the BGY fluorescent material adhered to each object to be sorted 10 can be calculated based on the existence range of the entire shell of each object to be sorted 10.

(2) In the above embodiments, one or more in-shell pistachios which are the objects to be sorted 10 are placed on the conveyor belt CB, and the pass/fail determination is performed based on the two-dimensional image data DA obtained by photographing one side of the upper side of the object to be sorted 10. That is, when the same pass/fail determination is performed on one side of the lower side, there is a possibility that the object to be sorted 10 that can be identified as a defective product remains among the objects to be sorted 10 not identified as the defective products in the pass/fail determination on the one side of the upper side.

Therefore, as a preferred implementation, in each of the above-described embodiments, after the objects to be sorted 10 identified as the defective products by the pass/fail determination on one side of the upper side is removed, the remaining objects to be sorted 10 are turned upside down, and then the pass/fail determination described in each of the above-described embodiments is performed again.

As a way to turn the objects to be sorted 10 upside down, two belt conveyors are arranged in series, and a step (difference in height) of the belt surfaces of the connecting portions of the two belt conveyors is set larger than the major axis length of the object to be sorted 10. As a result, when the object to be sorted 10 moves from the higher side to the lower side of the belt surfaces, the object to be sorted 10 can be turned upside down at the step portion.

Furthermore, as another preferred implementation, instead of performing the pass/fail determination and removal when one or more in-shell pistachios, which are the objects to be sorted 10, are placed on the conveyor belt CB, while one or more objects to be sorted 10 are falling in the air, the object to be sorted 10 falling in the air is irradiated from one side with ultraviolet light and the one side is photographed, and the object to be sorted 10 falling in the air is also irradiated from the other side with ultraviolet light and the other side is photographed, so that the pass/fail determination is performed on the both left and right sides of the objects to be sorted 10, and the objects to be sorted 10 identified as the defective products may be removed by blowing compressed air with an air gun or the like on the way to fall.

(3) In the seventh embodiment, an implementation has been described in which the remover 40 is configured with the parallel link robot, but the pick-up unit may be moved by a mechanism other than the parallel link robot. For example, the position of the pickup portion in the moving direction of the conveyor belt CB may be fixed, the positions of the one or more pickup portions in the width direction may be adjusted in accordance with the coordinates of the defective products, and when the object to be sorted 10 identified as the defective product moves below the pickup portion, the shutter of the pickup portion may open to suck and remove the object to be sorted 10.

INDUSTRIAL APPLICABILITY

The present invention is applicable to a pistachio sorting device for sorting in-shell pistachios using BGY fluorescence.

DESCRIPTION OF SYMBOLS

1-4: pistachio sorting device
10: object to be sorted (in-shell pistachio)
11, 21: lighting device (ultraviolet LED)
12, 22: optical filter
13: sensor (area camera)
14, 24: determining device
15: lightproof box (light shielding part)
23: sensor (line sensor)
31: lighting device
32: light source (ultraviolet semiconductor laser)
33: polygon mirror
34, 35: Fθ lens
36: reflecting mirror
40: remover
50: system for pistachio sorting device
51: processor
52: storage device
53: output interface
54: LED driver
55: input/output interface
56: robot interface
57: external storage interface
58: external storage device
CB: conveyor belt
D1: various data obtained by procedure for determination process
D2: coordinate data of center coordinates (coordinates of defective products)
DA: two-dimensional image data
IA: inspection region
LB0-LB 2: laser light
P1: control program
P2: determination processing program

The invention claimed is:

1. A pistachio sorting device for sorting one or more in-shell pistachios, which are objects to be sorted, by detecting a fluorescent material adhered to a shell of an in-shell pistachio to determine a pass/fail for each object to be sorted, the pistachio sorting device comprising:
a lighting device for irradiating the objects to be sorted in an inspection region with ultraviolet light having a maximum peak wavelength within a range of 345 nm to 390 nm;
an optical filter for selectively transmitting light within a wavelength range of 500 nm to 600 nm;
a sensor for detecting a two-dimensional intensity distribution of fluorescence emitted from the objects to be sorted and transmitted through the optical filter to generate a two-dimensional image data indicating a two-dimensional intensity distribution of the fluorescence in the inspection region; and
a determining device for determining a pass/fail for each object to be sorted based on the two-dimensional image data.

2. The pistachio sorting device according to claim 1, including a light shielding part that configures an inspection region inside and blocks entry of ambient light into the inspection region from outside.

3. The pistachio sorting device according to claim 1, wherein the lighting device irradiates the objects to be sorted in the inspection region with ultraviolet light having a maximum peak wavelength within a range of 350 nm to 375 nm.

4. The pistachio sorting device according to claim 1, wherein the determining device is configured to determine the pass/fail for each object to be sorted, based on the two-dimensional image data, in accordance with an area ratio between an area of an entire shell of an object to be sorted and an adhesion area of the fluorescent material to which a fluorescence intensity indicated by each pixel value of the two-dimensional image data within an existence range of the entire shell of the object to be sorted is equal to or larger than a predetermined threshold value.

5. The pistachio sorting device according to claim 4, wherein the determining device is configured to perform pattern matching with a pre-registered geometric shape based on the two-dimensional image data, approximate an outer edge of the object to be sorted with the geometric shape, and calculate an area of the geometric shape as an area of the entire shell of the object to be sorted.

6. The pistachio sorting device according to claim 5, wherein when there is a plurality of the objects to be sorted in the inspection region, the determining device specifies a processing range excluding a range in which the object to be sorted that can be identified as the defective product cannot exist from the inspection region based on the two-dimensional image data, and the determining device performs the pattern matching in the processing range.

7. The pistachio sorting device according to claim 1, wherein the determining device is configured to determine the pass/fail for each object to be sorted, based on the two-dimensional image data, in accordance with a maximum value of a fluorescence intensity indicated by each pixel value of the two-dimensional image data of the objects to be sorted within an existence range of an entire shell of an object to be sorted in the inspection region.

8. The pistachio sorting device according to claim 7, wherein the determining device is configured to perform pattern matching with a pre-registered geometric shape based on the two-dimensional image data, approximate an outer edge of the object to be sorted with the geometric shape, and calculate an existence range of the geometric shape in the inspection region as an existence range of the entire shell of the object to be sorted.

9. The pistachio sorting device according to claim 8, wherein when there is a plurality of the objects to be sorted in the inspection region, the determining device specifies a processing range excluding a range in which the object to be sorted that can be identified as the defective product cannot exist from the inspection region based on the two-dimensional image data, and the determining device performs the pattern matching in the processing range.

10. The pistachio sorting device according to claim 1, wherein the determining device is configured to determine the pass/fail for each object to be sorted, based on the two-dimensional image data, in accordance with to an area ratio between an area of an entire shell of an object to be sorted and an adhesion area of the fluorescent material to which the fluorescence intensity indicated by each pixel value of the two-dimensional image data within an existence range of the entire shell of the object to be sorted is equal to or larger than a predetermined threshold value, and in accordance with a maximum value of the fluorescence intensity indicated by each pixel value of the two-dimensional image data of the objects to be sorted within the existence range of the entire shell of the object to be sorted in the inspection region.

11. The pistachio sorting device according to claim 10, wherein the determining device is configured to perform pattern matching with a pre-registered geometric shape based on the two-dimensional image data, approximate an outer edge of the object to be sorted with the geometric shape, and calculate an area of the geometric shape as an area of the entire shell of the object to be sorted.

12. The pistachio sorting device according to claim 10, wherein the determining device is configured to perform pattern matching with a pre-registered geometric shape based on the two-dimensional image data, approximate an outer edge of the object to be sorted with the geometric shape, and calculate an existence range of the geometric shape in the inspection region as an existence range of the entire shell of the object to be sorted.

13. The pistachio sorting device according to claim 1, wherein the determining device is configured to calculate a two-dimensional coordinate of a center of a geometric shape approximating an outer edge of an object to be sorted identified as a defective product for a coordinate of a defective product in a two-dimensional coordinate indicating a position of the object to be sorted identified as the defective product in the inspection region.

14. The pistachio sorting device according to claim 1, including a remover, wherein
the determining device is configured to calculate a two-dimensional coordinate indicating a position of an object to be sorted identified as a defective product in the inspection region as a coordinate of a defective product, and
the remover is configured to remove the object to be sorted identified as the defective product based on the coordinate of the defective product calculated by the determining device.

* * * * *